(12) United States Patent
Anderskewitz et al.

(10) Patent No.: US 8,759,386 B2
(45) Date of Patent: Jun. 24, 2014

(54) PYRAZOLE COMPOUNDS AS CRTH2 ANTAGONISTS

(75) Inventors: Ralf Anderskewitz, Laupheim (DE); Domnic Martyres, Biberach an der Riss (DE); Thorsten Oost, Biberach an der Riss (DE); Wolfgang Rist, Mittelbiberach (DE); Peter Seither, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 293 days.

(21) Appl. No.: 13/353,621

(22) Filed: Jan. 19, 2012

(65) Prior Publication Data
US 2013/0023576 A1  Jan. 24, 2013

(30) Foreign Application Priority Data
Jan. 24, 2011  (EP) .................... 11151876

(51) Int. Cl.
*A61K 31/4155* (2006.01)
*C07D 231/10* (2006.01)
*C07D 403/12* (2006.01)
*C07D 405/12* (2006.01)
*C07D 409/12* (2006.01)

(52) U.S. Cl.
CPC ............ *C07D 403/12* (2013.01); *C07D 405/12* (2013.01); *C07D 409/12* (2013.01)
USPC ....................... 514/406; 548/364.4; 548/364.7

(58) Field of Classification Search
USPC .............. 514/406; 548/364.4, 364.7
See application file for complete search history.

(56) References Cited

U.S. PATENT DOCUMENTS
2008/0039442 A1 * 2/2008 Blom et al. .................. 514/217

FOREIGN PATENT DOCUMENTS
WO  2010057118 A2  5/2010

OTHER PUBLICATIONS
International Search Report for PCT/EP2012/050830 mailed Mar. 20, 2012.

* cited by examiner

*Primary Examiner* — Samantha Shterengarts
(74) *Attorney, Agent, or Firm* — Michael P. Morris; Timothy X. Witkowski

(57) ABSTRACT

Pyrazole compounds of formula (Ia) or (Ib) and pharmaceutically acceptable salts thereof,

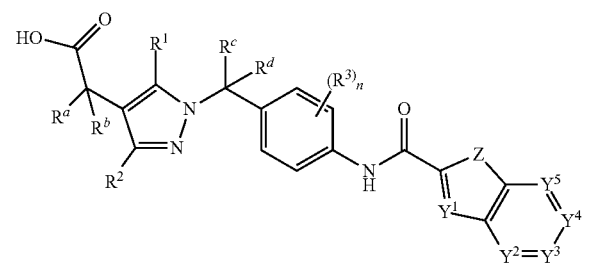
(Ia)

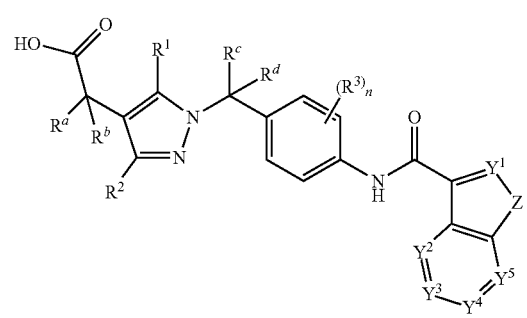

(Ib)

wherein $R^a, R^b, R^c, R^d, Y^1, Y^2, Y^3, Y^4, Y^5, Z, R^1, R^2$, n and $R^3$ have one of the meanings as indicated in the specification and claims, to their use as medicaments, to pharmaceutical formulations containing the compounds and to pharmaceutical formulations containing the compounds in combination with one or more active substances.

45 Claims, No Drawings

PYRAZOLE COMPOUNDS AS CRTH2 ANTAGONISTS

The present invention relates to pyrazole compounds of formula (Ia) or (Ib) and pharmaceutically acceptable salts thereof having CRTH2 antagonistic activity,

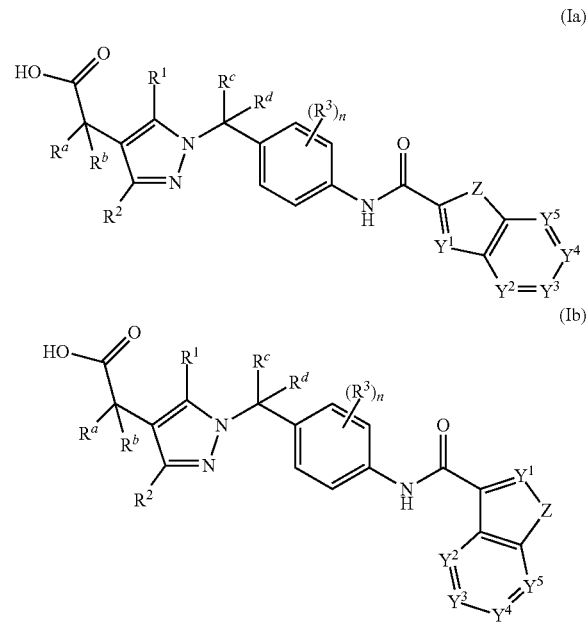

wherein $R^a$, $R^b$, $R^c$, $R^d$, $Y^1$, $Y^2$, $Y^3$, $Y^4$, $Y^5$, Z, $R^1$, $R^2$, n and $R^3$ have one of the meanings as indicated in the specification and claims, to their use as medicaments, to pharmaceutical formulations containing the compounds and to pharmaceutical formulations the compounds in combination with one or more active substances.

BACKGROUND OF THE INVENTION

Prostaglandin D2 (PGD2) is an eicosanoid generated by the metabolism of arachidonic acids upon stimulation of inflammatory cells with allergens, inflammatory stimuli or by tissue damage. PGD2 is primarily released by mast cells with Th2 cells, dendritic cells, and macrophages being secondary sources. PGD2 is the major arachidonic acid metabolite produced by mast cells upon allergen challenge (Lewis et al., J. Immunol. 1982, 129:1627-1631) and has been detected in high concentrations in the airways of asthmatic patients (Murray et al., N. Engl. J. Med., 1986, 315:800-804; Liu et al., Am. Rev. Respir. Dis., 1990, 142 126-132; Zehr et al., Chest, 1989, 95:1059-63; Wenzel et al., J. Allergy. Clin. Immunol., 1991, 87540-548). PGD2 production is also increased in patients with systemic mastocytosis (Roberts N. Engl. J. Med. 1980, 303, 1400-1404; Butterfield et al., Int Arch Allergy Immunol, 2008, 147:338-343) allergic rhinitis (Naclerio et al., Am. Rev. Respir. Dis., 1983, 128:597-602; Brown et al., Arch Otolaryngol Head Neck Surg, 1987, 113: 179-183; Lebel et al., J. Allergy Clin. Immunol., 1988, 82:869-877), urticaria (Heavy et al., J. Allergy. Clin. Immunol., 1986, 78:458-461), chronic rhinosinusitis (Yoshimura et al., Allergol. Int., 2008, 57:429-436), chronic obstructive pulmonary disease (Csanky et al., Electrophoresis, 2009, 30:1228-1234) and during anaphylaxis (Ono et al., Clin. Exp. Allergy, 2009, 39:72-80).

Instillation of PGD2 into airways can provoke features of asthmatic response including bronchoconstriction (Hardy et al., 1984, N Engl J. Med 311:209-213; Sampson et al. 1997, Thorax 52: 513-518) and eosinophil accumulation (Emery et al., 1989, J. Applied Physiol 67: 959-962). The potential of PGD2 to trigger inflammatory responses has been confirmed by the overexpression of human PGD2 synthase in mice resulting in elevated eosinophil lung inflammation and Th2 cytokine production in response to allergen (Fujitani et al., 2002 J. Immunol. 168:443-449).

PGD2 is an agonist of two 7-transmembrane type G protein-coupled receptors, the PGD2 receptor DP1 (Boie et al., J Biol Chem, 1995, 270:18910-6) and the recently identified CRTH2 (chemoattractant receptor-homologous molecule expressed on Th2 cells) receptor (also referred to as DP2 receptor) (Nagata et al., J. Immunol., 1999, 162:1278-86).

CRTH2 is expressed on Th2 cells, eosinophils, basophils and mast cells (Nagata et al., FEBS Lett, 1999, 459: 195-199; Nagata et al., J Immunol, 1999, 162: 1278-1286; Cosmi et al., Eur J Immunol, 2000, 30:2972-2979; Boehme et al., Int Immunol, 2009, 21: 621-32). Using selective CRTH2 agonists like 13,14 dihydro-15-keto-PGD2 (DK-PGD2) and 15R-methyl-PGD2, it has been shown that CRTH2 activation initiates cellular processes that lead to the recruitment and activation of inflammatory cells (Spik et al., J. Immunol., 2005; 174:3703-8; Shiraishi, J. Pharmacol. Exp. Ther., 2005, 312:954-60; Monneret et al., J. Pharmacol. Exp. Ther., 2003, 304:349-355). Using CRTH2 selective antagonists it has been shown that inflammatory responses and pathophysiological changes in animal models of diseases like asthma, allergic rhinitis, atopic dermatitis and COPD can be diminished (Uller et al., Respir Res. 2007, 8:16; Lukacs et al., Am. J. Physiol. Lung Cell Mol. Physiol. 2008, 295:L767-79; Stearns, Bioorg. Med. Chem. Lett. 2009, 19:4647-51; Nomiya, J Immunol, 2008, 180:5680-5688; Boehme et al., Int. Immunol., 2009, 21:1-17; Boehme et al., Int Immunol, 2009, 21:81-93; Takeshita et al., Int Immunol, 2004, 16:947-59; Stebbins et al., J. Pharmacol. Exp. Ther. 2009). Moreover, genetic deletion of CRTH2 in mice diminished inflammatory responses in animal models of allergy (Shiraishi et al., J. Immunol. 2008; 180:541-549; Oiwa, Clin Exp Allergy, 2008, 38:1357-66; Satoh et al., J. Immunol., 2006, 177:2621-9). In contrast, the selective DP1 agonist BW245C does not promote inflammatory responses, like migration or activation of Th2 lymphocytes, basophils or eosinophils (Yoshimura-Uchiyama et al., Clin. Exp. Allergy, 2004, 34:1283-90; Xue et al., Immunol, 2005, 175:6531-6; Gervais et al., J. Allergy Clin. Immunol., 2001, 108:982-8). Therefore, agents that antagonize the effects of PGD2 at the CRTH2 receptor should be useful for the treatment of respiratory or gastrointestinal complaints, as well as inflammatory diseases of the joints and allergic diseases of the nasopharynx, eyes and skin.

WO 2004/096777 teaches pyrimidine derivatives of formula (a) and salts thereof,

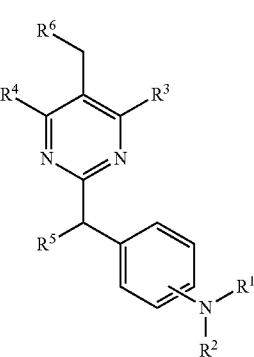

wherein R⁶ is carboxy, carboxamide, nitrile or tetrazolyl, the derivatives having CRTH2 antagonistic activity and can be used for the prophylaxis and treatment of diseases associated with CRTH2 activity.

WO 2009/042138 claims alkylthio substituted pyrimidine compounds of formula (b),

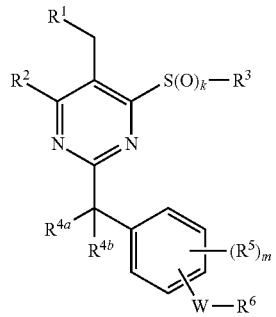

(b)

the compounds having CRTH2 antagonistic activity.

WO 2009/042139 claims 2-S-benzyl pyrimidine compounds of formula (c),

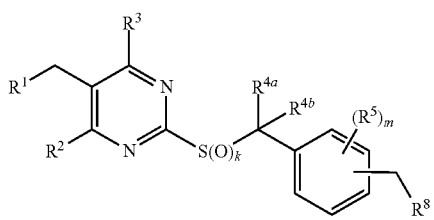

(c)

the compounds having CRTH2 antagonistic activity.

EP 0 480 659 claims compounds of general formula (d),

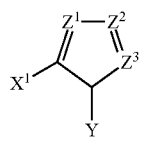

(d)

wherein $Z^2$ inter alia may be carboxyl-$C_1$-$C_{10}$-alkyl-C= and Y may be substituted benzyl, the compounds being useful for the treatment of hyperuricemia.

WO 2005/040128 claims compounds of general formula (e),

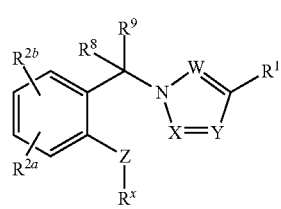

(e)

the compounds being useful for the treatment of conditions such as pain, or an inflammatory, immunological, bone, neurodegenerative or renal disorder.

WO 01/38325 claims compounds of general formula (f),

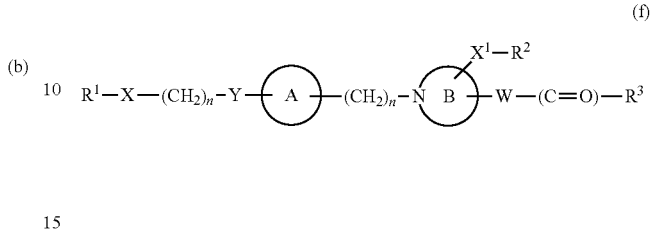

(f)

wherein A is an aromatic ring and B is a nitrogen-containing 5-membered hetero ring which may further be substituted, the compounds having hypoglycemic and hypolipidemic activity.

It is an objective of the present invention to provide further compounds having CRTH2 antagonistic activity.

Preferably the compounds of the present invention have enhanced chemical stability, enhanced pharmacokinetic properties (PK) and/or enhanced activity in a whole cell assay.

DETAILED DESCRIPTION OF THE INVENTION

The present invention relates to pyrazole compounds of formula (Ia) or (Ib) and pharmaceutically acceptable salts thereof,

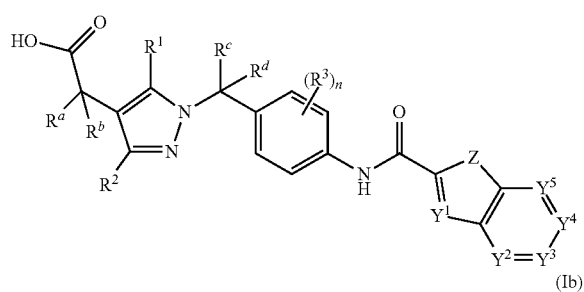

(Ia)

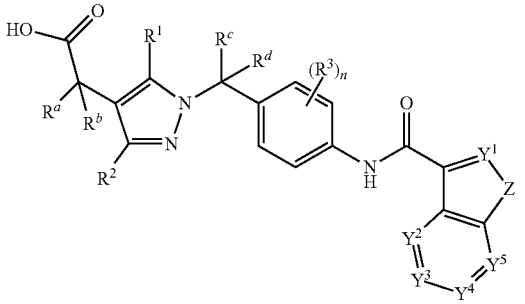

(Ib)

wherein:
$R^a$ and $R^b$ are independently selected hydrogen, hydroxy, halogen, $C_1$-$C_6$-alkyl, $C_1$-$C_6$ haloalkyl, $C_1$-$C_6$-alkoxy, $C_1$-$C_6$-haloalkoxy and $C_3$-$C_8$-cycloalkyl, or $R^a$ and $R^b$ together with the carbon atom they are bound to form may form a carbonyl group, or $R^a$ and $R^b$ together with the carbon atom they are bound to form a 3- to 8-membered ring, wherein the ring may contain 1 or 2 heteroatoms selected from O, N and S as ring member and wherein the ring members of the ring may optionally be independently substituted by hydroxy, halogen, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl;

$R^c$ and $R^d$ are independently selected hydrogen, hydroxy, halogen, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl, or $R^a$ and $R^b$ together with the carbon atom they are bound to form may form a carbonyl group, or Ra and Rb together with the carbon atom they are bound to form a 3- to 8-membered ring, wherein the ring may contain 1 or 2 heteroatoms selected from O, N and S as ring members and wherein the ring members of the ring may optionally be independently substituted by hydroxy, halogen, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl;

$Y^1$, $Y^2$, $Y^3$, $Y^4$ and $Y^5$ are independently selected from N and $CR^y$, wherein each $R^y$ is independently selected from H, hydroxy, halogen, cyano, nitro, $SF_5$, $C(O)NR^fR^g$, $C_1$-$C_6$-alkyl, hydroxy-$C_1$-$C_6$-alkyl, $C_1$-$C_6$-alkoxy-$C_1$-$C_6$-alkyl, $C_3$-$C_8$-cycloalkyl, $C_1$-$C_6$-haloalkyl, $C_1$-$C_6$-alkoxy, $C_1$-$C_6$-alkoxy-$C_1$-$C_6$-alkoxy, $C_1$-$C_6$-haloalkoxy, $C_3$-$C_8$-cycloalkoxy, $C_1$-$C_6$-alkylamino, di-$C_1$-$C_6$-alkylamino, $C_1$-$C_6$-alkylsulfonyl, phenyl, phenoxy, 5- or 6-membered heterocyclyl and 5- or 6-membered heterocyclyloxy, wherein $R^f$ and $R^g$ are independently from each other selected from H, $C_1$-$C_6$-alkyl, $C_1$-$C_6$-haloalkyl, $C_3$-$C_8$-cycloalkyl, $C_3$-$C_8$-cycloalkenyl and 5- or 6-membered heterocyclyl or $R^f$ and $R^g$ together with the nitrogen atom to which they are bound form a cyclic amine, which may comprise a further heteroatom selected from O, N and S as a ring member;

Z is selected from O, S and $NR^z$, wherein $R^z$ is H, $C_1$-$C_6$-alkyl or benzyl;

$R^1$ and $R^2$ are independently from each other selected from H, halogen, $C_1$-$C_6$-alkyl, $C_2$-$C_6$-alkenyl, $C_2$-$C_6$-alkynyl, $C_1$-$C_6$-alkoxy, $C_1$-$C_6$-alkylthio, —$NR^fR^g$, $C_3$-$C_8$-cycloalkyl, $C_3$-$C_8$-cycloalkyl-$C_1$-$C_6$-alkyl, $C_3$-$C_8$-cycloalkyl-$C_2$-$C_6$-alkenyl, $C_3$-$C_8$-cycloalkenyl, $C_3$-$C_8$-cycloalkenyl-$C_1$-$C_6$-alkyl, $C_3$-$C_8$-cycloalkenyl-$C_2$-$C_6$-alkenyl, phenyl, phenyl-$C_1$-$C_6$-alkyl, phenyl-$C_2$-$C_6$-alkenyl, naphthyl, naphthyl-$C_1$-$C_6$-alkyl, naphthyl-$C_2$-$C_6$-alkenyl, heterocyclyl, heterocyclyl-$C_1$-$C_6$-alkyl, and heterocyclyl-$C_2$-$C_6$-alkenyl, wherein the $C_1$-$C_6$-alkyl, $C_2$-$C_6$-alkenyl and $C_2$-$C_6$-alkynyl moieties in the aforementioned radicals $R^1$ and $R^2$ are unsubstituted or carry at least one substituent selected from hydroxy, halogen, cyano, nitro, $C_1$-$C_6$-alkoxy, $C_1$-$C_6$-haloalkoxy, $C_1$-$C_6$-alkylamino, di $C_1$-$C_6$-alkylamino and $C_1$-C6-alkylsulfonyl and/or
wherein two radicals bound to the same carbon atom of the $C_1$-$C_6$-alkyl, $C_2$-$C_6$-alkenyl and $C_2$-$C_6$-alkynyl moieties in the aforementioned radicals $R^1$ and $R^2$ together with the carbon atom may form a carbonyl group, and wherein the $C_3$-$C_8$-cycloalkyl, cycloalkenyl, phenyl, naphthyl and heterocyclyl moieties in the aforementioned radicals $R^1$ and $R^2$ are unsubstituted or carry at least one substituent selected from hydroxy, halogen, cyano, nitro, $C_1$-$C_6$-alkyl, $C_3$-$C_8$-cycloalkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, $C_1$-$C_6$-alkylsulfonyl, phenyl and 5- or 6-membered hetaryl and/or wherein two radicals bound to the same carbon atom of the $C_3$-$C_8$-cycloalkyl, $C_3$-$C_8$-cycloalkenyl and heterocyclyl moieties of the radicals $R^1$ and $R^2$ together with the carbon atom may form a carbonyl group, and wherein $R^f$ and $R^g$ are independently from each other selected from H, $C_1$-$C_6$-alkyl, $C_1$-$C_6$-haloalkyl, $C_3$-$C_8$-cycloalkyl, $C_3$-$C_8$-cycloalkenyl and heterocyclyl or $R^f$ and $R^g$ together with the nitrogen atom to which they are bound form a cyclic amine, which may comprise a further heteroatom selected from O, N and S as a ring member;

n is an integer selected from 0, 1, 2 or 3; and $R^3$ if present are selected independently from each other from halogen, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl.

Surprisingly it has been found that the compounds of formula (Ia) or (Ib) according to the present invention have significant CRTH2 antagonistic activity. Further it has been found that the compounds generally have enhanced chemical stability, enhanced pharmacokinetic properties (PK) and/or enhanced activity in a whole cell assay.

Thus the pyrazole compounds of formula (Ia) or (Ib) according to the present invention are suitable for the prevention and/or treatment of diseases related to CRTH2-activity.

Accordingly the present invention further relates to the use of pyrazole compounds of formula (Ia) or (Ib) according to the present invention as medicaments.

Furthermore the present invention relates to the use of compounds of formula (Ia) or (Ib) for preparing a medicament for the treatment of diseases related to CRTH2-activity. More specifically the present invention relates to the use of pyrazole compounds of formula (Ia) or (Ib) for preparing a medicament for the prevention and/or treatment of inflammatory, infectious and immunoregulatory disorders, respiratory or gastrointestinal diseases or complaints, inflammatory diseases of the joints and allergic diseases of the nasopharynx, eyes, and skin.

The present invention further relates to compounds of formula (Ia) or (Ib) according to the invention for treating and/or preventing diseases related to CRTH2-activity More specifically the present invention relates to compounds of formula (Ia) or (Ib) for use as a medicament for treating diseases related to CRTH2-activity. More specifically the present invention relates to pyrazole compounds of formula (Ia) or (Ib) for use as a medicament for the prevention and/or treatment of inflammatory, infectious and immunoregulatory disorders, respiratory or gastrointestinal diseases or complaints, inflammatory diseases of the joints and allergic diseases of the nasopharynx, eyes, and skin.

Furthermore the present invention relates to pharmaceutical formulations, containing one or more of the pyrazole compounds of formula (Ia) or (Ib) according to the present invention as sole active substance or in combination with one or more active substances selected from among betamimetics, anticholinergics, corticosteroids, PDE4 inhibitors, LTD4 antagonists, EGFR inhibitors, CCR3 antagonists, CCR5 antagonists, CCR9 antagonists, 5-LO inhibitors, histamine-receptor antagonists, SYK inhibitors and sulfonamides.

The activity in a whole cell eosinophil shape change assay of the compounds of the invention can be determined, for example, according to the following references: (i) Mathiesen J M, Ulven T, Martini L, Gerlach L O, Heinemann A, Kostenis E, Identification of indol derivatives exclusively interfering with a G protein-independent signalling pathway of the prostaglandin D2 receptor CRTH2. Mol. Pharmacol. 2005 August; 68(2):393-402; (ii) Schuligoi R, Schmidt R, Geisslinger G, Kollroser M, Peskar B A, Heinemann A. PGD2 metabolism in plasma: kinetics and relationship with bioactivity on DP1 and CRTH2 receptors. Biochem Pharmacol.

2007 Jun. 30; 74(1):107-17; (iii) Royer J F, Schratl P, Carrillo J J, Jupp R, Barker J, Weyman-Jones C, Beri R, Sargent C, Schmidt J A, Lang-Loidolt D, Heinemann A, A novel antagonist of prostaglandin D2 blocks the locomotion of eosinophils and basophils. Eur J Clin Invest. 2008 September; 38(9):663-71.

The chemical stability of the compounds of the invention can be determined, for example, under the following conditions: (i) 3 days incubation at 60° C. in 0.1 N HCl (hydrolytic stability under acidic conditions); (ii) 3 days incubation at 60° C. in pH 4.0 buffer solution (hydrolytic stability under weakly acidic conditions); (iii) 3 days incubation at 60° C. in pH 7.4 buffer solution (hydrolytic stability at physiological pH); (iv) 3 days incubation at 20° C. in 0.3% hydrogen peroxide (stability against oxidants); (v) 24 h incubation under UV-radiation (lambda=300-800 nm, P=250 W/m2) in water (stability against light). The kinetics of degradation can, for example, be determined by HPLC analysis.

The pharmacokinetic properties (PK) of the compounds of the invention can be determined in pre-clinical animal species, for example, mouse, rat, dog, guinea pig, mini pig, cynomolgus monkey, rhesus monkey. The pharmacokinetic properties of a compound can be described, for example, by the following parameters: Mean residence time, half-life, volume-of-distribution, AUC (area under the curve), clearance, bioavailability after oral administration.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals or moieties defined below, the number of carbon atoms is often specified preceding the group. As an example "$C_1$-$C_6$-alkyl" means an alkyl group or radical having 1 to 6 carbon atoms.

In general, for groups comprising two or more subgroups, the last named group is the radical attachment point.

Unless otherwise specified, conventional definitions of terms control and conventional stable atom valences are presumed and achieved in all formulas and groups.

In general all tautomeric forms and isomeric forms and mixtures, whether individual geometric isomers or optical isomers or racemic or non-racemic mixtures of isomers of a chemical structure or compound, are comprised, unless the specific stereochemistry or isomeric form is specifically indicated in the compound name or structure.

The term "substituted" as used herein, means that any one or more hydrogens on the designated atom, moiety or radical is replaced with a selection from the indicated group of radicals, provided that the designated atom's normal valence is not exceeded, and that the substitution results in a stable compound.

The compounds disclosed herein can exist as pharmaceutically acceptable salts. The present invention includes compounds in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCH, Zurich, Switzerland, 2002).

The term "pharmaceutically acceptable salt," as used herein, represents salts or zwitterionic forms of the compounds disclosed herein which are water or oil-soluble or dispersible and pharmaceutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphor sulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylene sulfonate, methane sulfonate, naphthylene sulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric acid, hydrobromic acid, sulfuric acid and phosphoric acid, and organic acids such as oxalic acid, maleic acid, succinic acid and citric acid. Salts can also be formed by coordination of the compounds with an alkali metal or alkaline earth ion. Hence, the present invention comprises sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine and piperazine.

While it may be possible for the compounds of the present invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carrier and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers and excipients may be used as suitable and as understood in the art; e.g. in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The term "halogen" as used herein denotes a halogen substituent selected from fluoro, chloro, bromo or iodo.

The term "$C_1$-$C_6$-alkyl" as used herein (including the alkyl moieties of $C_1$-$C_6$-alkoxy, $C_1$-$C_6$-alkylamino, di-$C_1$-$C_6$-alkylamino, $C_1$-$C_6$-alkylthio and the like) denotes branched and unbranched alkyl moieties with 1 to 6 carbon atoms attached to the remaining compound at any position of the alkyl chain. The term "$C_1$-$C_4$-alkyl" accordingly denotes a branched or unbranched alkyl moiety with 1 to 4 carbon atoms. "$C_1$-$C_4$-alkyl" is generally preferred. Examples of "$C_1$-$C_6$-alkyl" include: methyl, ethyl, n-propyl, isopropyl, n-butyl, isobutyl, sec-butyl, tert-butyl, n-pentyl, isopentyl, neopentyl or hexyl. Unless stated otherwise, the definitions propyl, butyl, pentyl and hexyl include all the possible isomeric forms of the groups in question. Thus, for example, propyl includes n-propyl and isopropyl, butyl includes isobutyl, sec-butyl and tert-butyl etc.

The term "$C_1$-$C_6$-haloalkyl" as used herein (including the alkyl moieties of $C_1$-$C_6$-haloalkoxy, $C_1$-$C_6$-haloalkylamino, di-$C_1$-$C_6$-haloalkylamino, $C_1$-$C_6$-haloalkylthio and the like) denotes branched and unbranched alkyl moieties with 1 to 6 carbon atoms wherein one or more hydrogen atoms are replaced by a halogen atom selected from among fluorine, chlorine or bromine, preferably fluorine and chlorine, particularly preferably fluorine. The term "$C_1$-$C_4$-haloalkyl" accordingly denotes branched and unbranched alkyl moieties with 1 to 4 carbon atoms, wherein one or more hydrogen atoms are replaced analogously to what was stated above. $C_1$-$C_4$-haloalkyl is generally preferred. Preferred examples include: $CH_2F$, $CHF_2$ and $CF_3$.

The term "$C_2$-$C_6$-alkenyl" as used herein (including the alkenyl moieties of other radicals) denotes branched and unbranched alkenyl groups with 2 to 6 carbon atoms attached to the remaining compound at any position of the alkenyl chain and having at least one double bond. The term "$C_2$-$C_4$-alkenyl" accordingly denotes branched and unbranched alkenyl moieties with 2 to 4 carbon atoms. Preferred are alkenyl moieties with 2 to 4 carbon atoms. Examples include: ethenyl or vinyl, propenyl, butenyl, pentenyl or hexenyl. Unless otherwise stated, the definitions propenyl, butenyl, pentenyl and hexenyl include all possible isomeric forms of the moieties in question. Thus, for example, propenyl includes 1-propenyl and 2-propenyl, butenyl includes 1-, 2- and 3-butenyl, 1-methyl-1-propenyl, 1-methyl-2-propenyl etc.

The term "$C_2$-$C_6$-alkynyl" as used herein (including the alkynyl moieties of other radicals) denotes branched and unbranched alkynyl groups with 2 to 6 carbon atoms attached to the remaining compound at any position of the alkynyl chain and having at least one triple bond. The term "$C_2$-$C_4$-alkynyl" accordingly denotes branched and unbranched alkynyl moieties with 2 to 4 carbon atoms. Alkynyl moieties with 2 to 4 carbon atoms are preferred. Examples include: ethynyl, propynyl, butynyl, pentynyl, or hexynyl. Unless otherwise stated, the definitions propynyl, butynyl, pentynyl and hexynyl include all the possible isomeric forms of the respective moieties. Thus, for example, propynyl includes 1-propynyl and 2-propynyl, butynyl includes 1-, 2- and 3-butynyl, 1-methyl-1-propynyl, 1-methyl-2-propynyl etc.

The term "$C_3$-$C_8$-cycloalkyl" as used herein (including the cycloalkyl moieties of other radicals) denotes cyclopropyl, cyclobutyl, cyclopentyl, cyclohexyl, cycloheptyl and cyclooctyl.

Preferred are cyclic alkyl groups with 3 to 6 carbon atoms, such as cyclopropyl, cyclopentyl and cyclohexyl.

The term "$C_3$-$C_8$-cycloalkenyl" as used herein (including the cycloalkenyl moieties of other radicals) denotes carbocyclic radicals having 3 to 8 carbon atoms and containing at least one, preferably one or two, non-conjugated double bonds. Examples are cyclopentenyl, cyclopantadienyl, cyclohexenyl and cyclohexadienyl.

The term "heterocyclyl" as used herein (including the heterocyclyl moieties of other radicals) denotes 5- to 7-membered heterocyclic radicals and 5- to 10-membered, bicyclic heterocyclic radicals, containing one, two or three heteroatoms, selected from O, N and S as ring members. The heterocyclyl may be linked to the molecule by a carbon atom or, if present, by a nitrogen atom. The term "heterocyclyl" as used herein encompasses saturated or partially unsaturated heterocyclyl as well as hetaryl.

The term "saturated or partially unsaturated heterocyclyl" as used herein (including the heterocyclyl moieties of other radicals) denotes 5- to 7-membered monocyclic heterocyclic radicals as defined above containing a number of double bonds such that no aromatic system is formed as well as 5- to 10-membered bicyclic heterocyclic radicals as defined above containing a number of double bonds such that no aromatic system is formed in at least one of the cycles.

Examples of monocyclic saturated or partially unsaturated heterocyclyl include pyrrolidine, tetrahydrofurane, tetrahydrothiophene, thiazolidine, dioxolane, piperidine, tetrahydropyrane, tetrahydrothiopyrane, piperazine, morpholine, thiomorpholine, oxazepane, and the like.

Examples of bicyclic saturated or partially unsaturated heterocyclyl include dihydropyrrolizine, pyrrolizine, tetrahydroquinoline, tetrahydroisoquinoline, tetrahydroimidazopyridine, tetrahydropyrazolopyridine, benzopyrane, benzodiazepine, and the like.

The term "hetaryl" as used herein (including the heterocyclyl moieties of other radicals) denotes 5- to 7-membered monocyclic heterocyclic radicals as defined above containing a number of double bonds such that an aromatic system is formed as well as 5- to 10-membered bicyclic heterocyclic radicals as defined above containing a number of double bonds such that an aromatic system is formed in both cycles.

Examples of monocyclic aromatic heterocyclyl include furan, thiazole, pyrrole, thiophene, pyrazole, imidazole, thiadiazole, 1,2,3-triazole, 1,2,4-triazole, tetrazole, oxazole, oxadiazole, pyridine, pyridazine, pyrimidine, pyrazine, and the like.

Examples of bicyclic aromatic heterocyclyl include pyrrolizine, indole, indolizine, isoindole, indazole, purine, quinoline, isoquinoline, benzimidazole, benzofuran, benzothiazole, benzoisothiazole, pyridopyrimidine, pteridine, pyrimidopyrimidine, imidazopyridine, pyrazolopyridine, and the like.

The term "fused carbocyclic or heterocyclic moiety" as used herein denotes $C_3$-$C_8$-cycloalkyl, $C_3$-$C_8$-cycloalkenyl, benzene and heterocyclyl moieties as defined above, wherein the moieties share at least one bond with the cyclic moiety they are bound to. As an example benzene fused to benzene is naphthalene. Preferred are fused cyclic moieties sharing one bond with the cyclic moiety they are fused to. Further preferred the fused moiety is benzene.

The term "3- to 8-membered ring formed by two radicals together with the carbon atom they are bound, wherein the ring may contain 1 or 2 heteroatoms selected from O, N and S as ring member" as used herein denotes $C_3$-$C_8$-cycloalkyl, $C_3$-$C_8$-cycloalkenyl and heterocyclyl moieties as defined above.

The term "cyclic amine formed by two radicals together with the nitrogen atom to which they are bound, wherein the ring may comprise a further heteroatom selected from O, N and S as a ring member" as used herein denotes cyclic amines having 3 to 8, preferably 5 or 6, ring members. Examples of such formed amines are pyrrolidine, piperidine, piperazine, morpholine, pyrrole, imidazole, and the like.

The terms "heterocyclyl-$C_1$-$C_6$-alkyl", "$C_3$-$C_8$-cycloalkyl-$C_1$-$C_6$-alkyl", "phenyl-$C_1$-$C_6$-alkyl" and "naphthyl-$C_1$-$C_6$-alkyl" as used herein denote alkyl moieties as defined above having 1 to 6 carbon atoms, wherein any one of the hydrogen atoms is replaced by a cyclic moiety as defined above. In these terms the alkyl moiety preferably has 1 to 4 carbon atoms ($C_1$-$C_4$-alkyl). More preferably the alkyl moiety is methyl or ethyl, and most preferred methyl. Preferred examples of phenyl-$C_1$-$C_6$-alkyl are benzyl or phenethyl.

The terms "heterocyclyl-$C_2$-$C_6$-alkenyl", "$C_3$-$C_8$-cycloalkyl-$C_2$-$C_6$-alkenyl", "phenyl-$C_2$-$C_6$-alkenyl" and "naphthyl-$C_2$-$C_6$-alkenyl" as used herein denote alkenyl moieties as defined above having 2 to 6 carbon atoms, wherein any one of the hydrogen atoms is replaced by a cyclic moiety as defined above. In these terms the alkenyl moiety preferably has 2 to 4 carbon atoms ($C_2$-$C_4$-alkenyl). More preferably the alkenyl moiety is ethenyl. A preferred example of phenyl-$C_2$-$C_6$-alkenyl is phenethenyl.

The specific and preferred definitions given for the individual radicals and moieties $R^a$, $R^b$, $R^c$, $R^d$, $Y^1$, $Y^2$, $Y^3$, $Y^4$, $Y^5$, $Z$, $R^1$, $R^2$, n and $R^3$ herein below are valuable on their own as well as in combination. As will be understood preferred are compounds of formula (Ia) or (Ib) wherein one or more of the individual radicals and moieties $R^a$, $R^b$, $R^c$, $R^d$, $Y^1$, $Y^2$, $Y^3$, $Y^4$, $Y^5$, $Z$, $R^1$, $R^2$, n and $R^3$ have one of the meanings indicated as preferred herein-below and wherein the remaining radicals and moieties are as specified hereinbefore. Most preferred are compounds of formula (Ia) or (Ib) wherein all of the individual radicals and moieties $R^a$, $R^b$, $R^c$, $R^d$, $Y^1$, $Y^2$, $Y^3$, $Y^4$, $Y^5$, $Z$, $R^1$, $R^2$, n and $R^3$ have one of the meanings indicated as preferred herein-below.

One particular embodiment of the invention relates to pyrazole compounds of formula (Ia), wherein the individual moieties have one of the meanings given in the specification. Preferred are compounds of formula (Ia), wherein the individual moieties have one of the preferred meanings given in the specification.

Another particular embodiment of the invention relates to pyrazole compounds of formula (Ib), wherein the individual moieties have one of the meanings given in the specification. Preferred are compounds of formula (Ib), wherein the individual moieties have one of the preferred meanings given in the specification.

Preferred are pyrazole compounds of formula (Ia) or (Ib), wherein $R^a$ and $R^b$ are independently selected hydrogen, $C_1$-$C_6$-alkyl, $C_1$-$C_6$ haloalkyl and $C_3$-$C_8$-cycloalkyl.

Particularly preferred are pyrazole compounds of formula (Ia) or (Ib), wherein $R^a$ and $R^b$ are both hydrogen.

Likewise preferred are pyrazole compounds of formula (Ia) or (Ib), wherein $R^c$ and $R^d$ are independently selected hydrogen, $C_1$-$C_6$-alkyl, $C_1$-$C_6$-haloalkyl and $C_3$-$C_8$-cycloalkyl.

Particularly preferred are pyrazole compounds of formula (Ia) or (Ib), wherein $R^c$ and $R^d$ are both hydrogen.

Likewise preferred are pyrazole compounds of formula (Ia) or (Ib), wherein $Y^1$ is $CR^{y1}$ or N, wherein $R^{y1}$ has one of the meanings given for $R^y$.

More preferred are pyrazole compounds of formula (Ia) or (Ib), wherein $Y^1$ is $CR^{y1}$, in particular wherein $R^{y1}$ is selected from H, $C_1$-$C_6$-alkyl, $C_1$-$C_6$-alkoxy-$C_1$-$C_6$-alkyl and $C_1$-$C_6$-haloalkyl.

Likewise preferred are pyrazole compounds of formula (Ia) or (Ib), wherein $Y^2$ is $CR^{y2}$, $Y^3$ is $CR^{y3}$, $Y^4$ is $CR^{y4}$ and/or $Y^5$ is $CR^{y5}$, wherein $R^{y2}$, $R^{y3}$, $R^{y4}$ and $R^{y5}$ independently from each other have one of the meanings as defined for $R^y$.

More preferred are pyrazole compounds of formula (Ia) or (Ib), wherein $Y^2$ is $CR^{y2}$, $Y^3$ is $CR^{y3}$, $Y^4$ is $CR^{y4}$ and $Y^5$ is $CR^{y5}$, wherein $R^{y2}$, $R^{y3}$, $R^{y4}$ and $R^{y5}$ independently from each other have one of the meanings as defined for $R^y$, in particular wherein $R^{y2}$, $R^{y3}$, $R^{y4}$ and $R^{y5}$ are independently selected from H, halogen, $C_1$-$C_6$-alkoxy, $C_1$-$C_6$-alkoxy-$C_1$-$C_6$-alkoxy and $C_1$-$C_6$-haloalkoxy.

One particular embodiment of the invention relates to pyrazole compounds of formula (Ia) or (Ib), wherein Z is O and the remaining moieties have one of the meanings given in the specification, preferably one of the preferred meanings given in the specification.

Another particular embodiment of the invention relates to pyrazole compounds of formula (Ia) or (Ib), wherein Z is S and the remaining moieties have one of the meanings given in the specification, preferably one of the preferred meanings given in the specification.

Another particular embodiment of the invention relates to pyrazole compounds of formula (Ia) or (Ib), wherein Z is $NR^z$, wherein $R^z$ is H, $C_1$-$C_6$-alkyl or benzyl, and the remaining moieties have one of the meanings given in the specification, preferably one of the preferred meanings given in the specification.

Likewise preferred are pyrazole compounds of formula (Ia) or (Ib), wherein $R^1$ and $R^2$ independently from each other are selected from H, $C_1$-$C_6$-alkyl, $C_3$-$C_8$-cycloalkyl, phenyl and naphthyl.

More preferred are pyrazole compounds of formula (Ia) or (Ib), wherein $R^1$ and $R^2$ independently from each other are selected from H, $C_1$-$C_4$-alkyl, $C_3$-$C_6$-cycloalkyl and phenyl.

Particularly preferred are pyrazole compounds of formula (Ia) or (Ib), wherein $R^1$ and $R^2$ are selected from $C_1$-$C_4$-alkyl.

Likewise preferred are pyrazole compounds of formula (Ia) or (Ib), wherein n is 0, 1, 2 or 3, in particular wherein n is 0 or 1.

Likewise preferred are pyrazole compounds of formula (Ia) or (Ib), wherein $R^3$ if present are independently selected from halogen, $C_1$-$C_6$-alkoxy and $C_1$-$C_6$-haloalkoxy.

More preferred are pyrazole compounds of formula (Ia) or (Ib), wherein $R^3$ if present are independently selected from halogen, in particular from F, Cl and Br.

One preferred particular embodiment of the invention relates to pyrazole compounds selected from compounds of formula (Ia'),

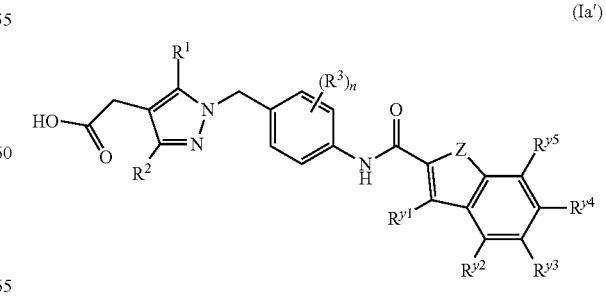

(Ia')

wherein Z, $R^1$, $R^2$, $R^3$, $R^{y1}$, $R^{y2}$, $R^{y3}$, $R^{y4}$ and $R^{y5}$ have one of the meanings given above and n is 0 or 1.

More preferred are pyrazole compounds (Ia') wherein at least one of the moieties Z, $R^1$, $R^2$, $R^3$, $R^{y1}$, $R^{y2}$, $R^{y3}$, $R^{y4}$ and $R^{y5}$ have one of the preferred meanings given above.

Another preferred particular embodiment of the invention relates to pyrazole compounds selected from compounds of formula (Ib'),

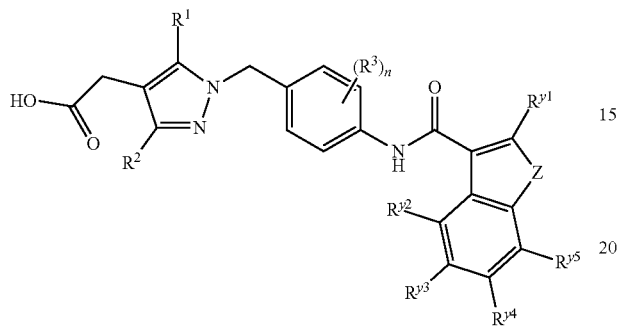

(Ib')

wherein Z, $R^1$, $R^2$, $R^3$, $R^{y1}$, $R^{y2}$, $R^{y3}$, $R^{y4}$, and $R^{y5}$ have one of the meanings given above.

More preferred are pyrazole compounds (Ia') wherein at least one of the moieties Z, $R^1$, $R^2$, $R^3$, $R^{y1}$, $R^{y2}$, $R^{y3}$, $R^{y4}$, and $R^{y5}$ have one of the preferred meanings given above.

A further embodiment of the present invention relates to compounds of formula (Ia) or (Ib), wherein the compounds of formula (Ia) or (Ib) are present in the form of the individual optical isomers, mixtures of the individual enantiomers or racemates, preferably in the form of the enantiomerically pure compounds.

A further embodiment of the present invention relates to compounds of formula (Ia) or (Ib), wherein the compounds of formula (Ia) or (Ib) are present in the form of the acid addition salts thereof with pharmacologically acceptable acids as well as optionally in the form of the solvates and/or hydrates.

Preparation

The compounds according to the invention may be obtained using methods of synthesis which are known to a person skilled in the art and described in the literature of organic synthesis. Preferably the compounds are obtained analogously to the methods of preparation explained more fully hereinafter, in particular as described in the experimental section.

Compounds of formula (Ia) according to the present invention can be prepared according to scheme 1.

Scheme 1

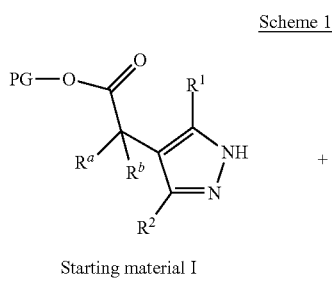

Starting material I

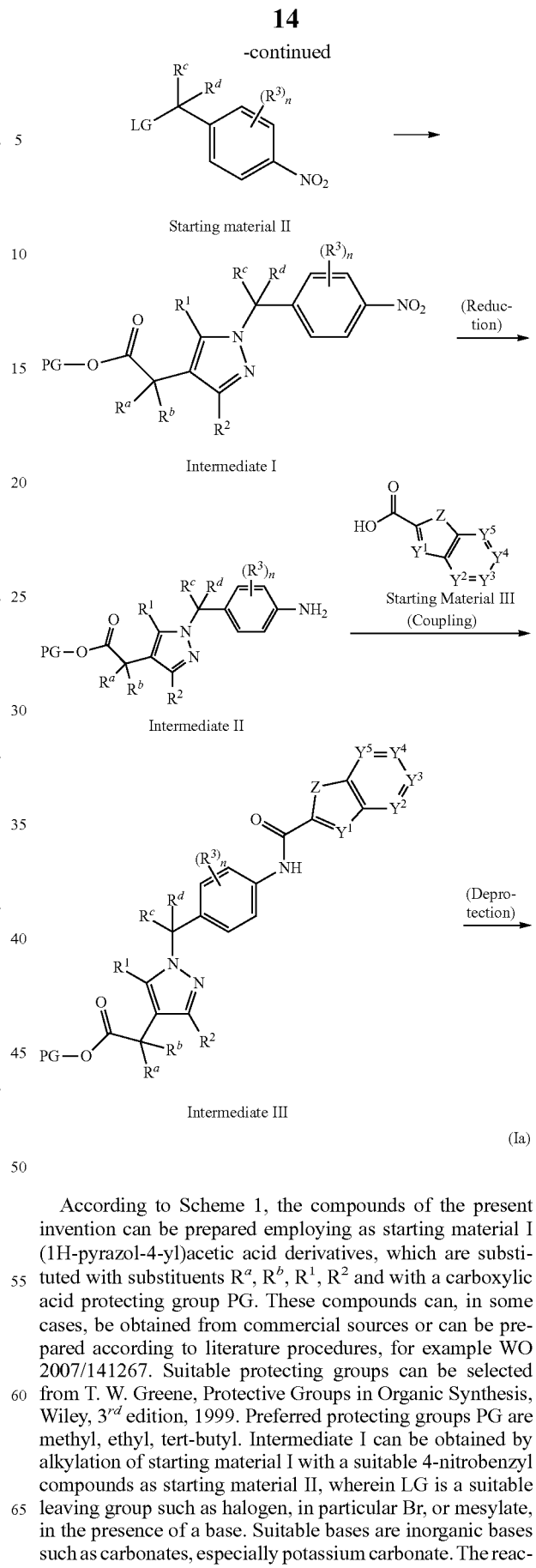

According to Scheme 1, the compounds of the present invention can be prepared employing as starting material I (1H-pyrazol-4-yl)acetic acid derivatives, which are substituted with substituents $R^a$, $R^b$, $R^1$, $R^2$ and with a carboxylic acid protecting group PG. These compounds can, in some cases, be obtained from commercial sources or can be prepared according to literature procedures, for example WO 2007/141267. Suitable protecting groups can be selected from T. W. Greene, Protective Groups in Organic Synthesis, Wiley, $3^{rd}$ edition, 1999. Preferred protecting groups PG are methyl, ethyl, tert-butyl. Intermediate I can be obtained by alkylation of starting material I with a suitable 4-nitrobenzyl compounds as starting material II, wherein LG is a suitable leaving group such as halogen, in particular Br, or mesylate, in the presence of a base. Suitable bases are inorganic bases such as carbonates, especially potassium carbonate. The reaction is preferably carried out in an organic solvent such as dimethylformamide, dimethylsulfoxide, acetonitrile, tetrahydrofuran, dichloromethane or a mixture of solvents. The reaction usually takes place within 1 to 48 hours. Preferred reaction temperatures are between 0° C. and the boiling point of the reaction mixture. When $R^1$ is different from $R^2$, the alkylation reaction may yield a mixture of regioisomers. The individual isomers may be separated by methods which are known to a person skilled in the art, for example, chromatography over silica gel employing a suitable solvent or solvent mixtures, or preparative reversed phase chromatography, employing a suitable gradient of solvents, or trituration or crystallization from suitable solvents or solvent mixtures Amine intermediate II can be prepared from intermediate I by reduction of the nitro group, for instance by hydrogenolysis in the presence of a catalyst, such as palladium on carbon or Raney Nickel. The reaction is preferably carried out in an inert organic solvent, such as methanol, ethanol, acetic acid, ethyl acetate or a mixture of solvents. The reaction usually takes place within 1 to 48 hours. Preferred reaction temperatures are between 0° C. and 50° C. Preferred reaction pressures are between atmospheric pressure and 100 bar. The reduction of the nitro group in intermediate II can also be carried out according to alternative methods described in J. March, Advanced Organic Chemistry, Wiley, $4^{th}$ edition, 1992, p. 1216-1217. Amide intermediate III can be prepared from amine intermediate II by coupling with a carboxylic acid (Starting Material III) in the presence of a coupling reagent, such as 2-(1H-benzotriazole-1-yl)-1,1,3,3-tetramethyluronium tetrafluoroborate (TBTU), and a base, such as diisopropylethylamine. The reaction is preferably carried out in an inert organic solvent, such as dimethylformamide, tetrahydrofuran, dichloromethane or a mixture of solvents. The reaction usually takes place within 1 to 48 hours. Preferred reaction temperatures are between 0° C. and 30° C. The coupling of a carboxylic acid to the amino group of intermediate III can also be carried out according to alternative methods described in J. March, Advanced Organic Chemistry, Wiley, $4^{th}$ edition, 1992, p. 419-421. Alternatively, instead of the carboxylic acid (starting material III) and a coupling reagent, the corresponding acyl chloride or anhydride may be employed.

Compounds of formula (Ia) can be obtained from intermediate III by removal of the protecting group PG. In the case the hydroxycarbonyl group is protected by $CH_3$ or $C_2H_5$, this conversion can be carried out under aqueous conditions in the presence of an inorganic base, such as NaOH or LiOH. The reaction is preferably carried out in water or a mixture of water with $CH_3OH$, $C_2H_5OH$, tetrahydrofuran or dioxane. The reaction usually takes place within 1 to 48 hours. Preferred reaction temperatures are between 0° C. and the boiling point of the reaction mixture. In the case that PG is tert-butyl, the deprotection can be carried out under acidic conditions, for instance with trifluoroacetic acid, hydrochloric acid or montmorillonite. When using trifluoroacetic acid, the reaction can be carried out in neat trifluoroacetic acid or in an inert solvent, such as dichloromethane. The reaction usually takes place within 1 to 48 hours. Preferred reaction temperatures are between 0° C. and 30° C. The cleavage of the protecting group PG may also be carried out according to alternative methods described in J. March, Advanced Organic Chemistry, Wiley, $4^{th}$ edition, 1992, p. 378-383 or in T. W. Greene, Protective Groups in Organic Synthesis, Wiley, $3^{rd}$ edition, 1999.

Compounds of formula (Ib) can be obtained following the procedure depicted in scheme I using starting material of formula III', wherein

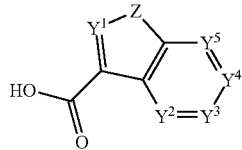

Starting material III'

$Y^1$, $Y^2$, $Y^3$, $Y^4$, $Y^5$ and Z have one of the meanings indicated above, instead of starting material III.

Indications

The compounds of formula (Ia) or (Ib) according to the present invention are especially useful for manufacturing a medicament for the prevention and/or treatment of diseases wherein the activity of a CRTH2-receptor is involved.

One embodiment of the present invention relates to the manufacturing of a medicament for the prevention and/or treatment of a wide variety of inflammatory, infectious, and immunoregulatory disorders, respiratory or gastrointestinal diseases or complaints, inflammatory diseases of the joints and allergic diseases of the nasopharynx, eyes, and skin. Such disorders diseases and complaints include asthma and allergic diseases, eosinophilic diseases, chronic obstructive pulmonary disease, infection by pathogenic microbes (which, by definition, includes viruses), as well as autoimmune pathologies, such as the rheumatoid arthritis and atherosclerosis.

Preferred is the manufacturing of a medicament for the prevention and/or treatment of inflammatory or allergic diseases and conditions, including allergic or non-allergic rhinitis or sinusitis, chronic sinusitis or rhinitis, nasal polyposis, chronic rhinosinusitis, acute rhinosinusitis, asthma, pediatric asthma, allergic bronchitis, alveolitis, Farmer's disease, hyperreactive airways, allergic conjunctivitis, bronchitis or pneumonitis caused by infection, e.g. by bacteria or viruses or helminthes or fungi or protozoans or other pathogens, bronchiectasis, adult respiratory distress syndrome, bronchial and pulmonary edema, bronchitis or pneumonitis or interstitial pneumonitis caused by different origins, e.g. aspiration, inhalation of toxic gases, vapors, bronchitis or pneumonitis or interstitial pneumonitis caused by heart failure, X-rays, radiation, chemotherapy, bronchitis or pneumonitis or interstitial pneumonitis associated with collagenosis, e.g. lupus erythematodes, systemic scleroderma, lung fibrosis, idiopathic pulmonary lung fibrosis (IPF), interstitial lung diseases or interstitial pneumonitis of different origin, including asbestosis, silicosis, m. Boeck or sarcoidosis, granulomatosis, cystic fibrosis or mucoviscidosis, or α1-antitrypsin deficiency, eosinophilic cellulites (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, non-allergic asthma; exercise induced bronchoconstriction; chronic obstructive pulmonary disease (COPD), acute bronchitis, chronic bronchitis, cough, pulmonary emphysema; systemic anaphylaxis or hypersensitivity responses, drug allergies (e.g., to penicillin, cephalosporin), eosinophilia-myalgia syndrome due to the ingestion of contaminated tryptophane, insect sting allergies; autoimmune diseases, such as rheumatoid arthritis, psoriatic arthritis, multiple sclerosis, systemic lupus erythematosus, myasthenia gravis, immune thrombocytopenia (adult ITP, neonatal thrombocytopenia, pediatric ITP), immune hemolytic anemia (auto-immune and drug induced), Evans syndrome (platelet and red cell immune cytopaenias), Rh disease of the newborn, Goodpasture's syndrome (anti-GBM disease), Celiac, autoimmune cardio-myopathy juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); erythema nodosum; eosinophilic myositis, eosinophilic fasciitis, cancers with leukocyte infiltration of the skin or organs.

Method of Treatment

Accordingly, the compounds of formula (Ia) or (Ib) according to the present invention are useful in the prevention and/or treatment of a wide variety of inflammatory, infectious, and immunoregulatory disorders and diseases. Such disorders and diseases include but are not limited to asthma and allergic diseases, chronic obstructive pulmonary disease, infection by pathogenic microbes (which, by definition, includes viruses), autoimmune pathologies such as the rheumatoid arthritis and atherosclerosis.

As an example, an instant compound of formula (Ia) or (Ib) which inhibits one or more functions of a mammalian CRTH2 receptor (e.g., a human CRTH2 receptor) may be administered to inhibit (i.e., reduce or prevent) inflammation and bronchoconstriction. As a result, one or more inflammatory processes, such as leukocyte emigration, adhesion, chemotaxis, exocytosis (e.g., of enzymes, growth factors, histamine, cytotoxic proteins), inflammatory mediator release, survival or proliferation of CRTH2 expressing cells is inhibited. For example, activation or recruitment of Th2 cells, mast cells, basophils and eosinophilic to inflammatory sites (e.g., in asthma or allergic rhinitis) can be inhibited according to the present method.

In particular, the compounds of the following examples have activity in blocking the activation and migration of cells expressing the CRTH2 receptor using the appropriate CRTH2 agonists in the aforementioned assays.

Diseases or conditions of humans which can be treated with inhibitors of CRTH2 receptor function, include, but are not limited to inflammatory or allergic diseases and conditions, including allergic or non-allergic rhinitis or sinusitis, chronic sinusitis or rhinitis, nasal polyposis, chronic rhinosinusitis, acute rhinosinusitis, asthma, pediatric asthma, allergic bronchitis, alveolitis, Farmer's disease, hyperreactive airways, allergic conjunctivitis, bronchitis or pneumonitis caused by infection, e.g. by bacteria or viruses or helminthes or fungi or protozoans or other pathogens, bronchiectasis, adult respiratory distress syndrome, bronchial and pulmonary edema, bronchitis or pneumonitis or interstitial pneumonitis caused by different origins, e.g. aspiration, inhalation of toxic gases, vapors, bronchitis or pneumonitis or interstitial pneumonitis caused by heart failure, X-rays, radiation, chemotherapy, bronchitis or pneumonitis or interstitial pneumonitis associated with collagenosis, e.g. lupus erythematodes, systemic scleroderma, lung fibrosis, idiopathic pulmonary lung fibrosis (IPF), interstitial lung diseases or interstitial pneumonitis of different origin, including asbestosis, silicosis, m. Boeck or sarcoidosis, granulomatosis, cystic fibrosis or mucoviscidosis, or α1-antitrypsin deficiency, eosinophilic cellulites (e.g. Well's syndrome), eosinophilic pneumonias (e.g. Loeffler's syndrome, chronic eosinophilic pneumonia), eosinophilic fasciitis (e.g. Shulman's syndrome), delayed-type hypersensitivity, non-allergic asthma, exercise induced bronchoconstriction; chronic obstructive pulmonary disease (COPD), acute bronchitis, chronic bronchitis, cough, pulmonary emphysema; systemic anaphylaxis or hypersensitivity responses, drug allergies (e.g., to penicillin, cephalosporin), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, immune thrombocytopenia (adult ITP, neonatal thrombocytopenia, pediatric ITP), immune hemolytic anemia (auto-immune and drug induced), Evans syndrome (platelet and red cell immune cytopaenias), Rh disease of the newborn, Goodpasture's syndrome (anti-GBM disease), Celiac, autoimmune cardio-myopathy juvenile onset diabetes; glomerulonephritis, autoimmune thyroiditis, Behcet's disease; graft rejection (e.g. in transplantation), including allograft rejection or graftversus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g. necrotizing, cutaneous, and hypersensitivity vasculitis); erythema nodosum; eosinophilic myositis, eosinophilic fasciitis; cancers with leukocyte infiltration of the skin or organs.

Combinations

The compounds of formula (Ia) or (Ib) according to the present invention may be used on their own or in combination with other compounds of formula (Ia) or (Ib). The compounds of formula (Ia) or (Ib) may optionally also be combined with other pharmacologically active substances.

Such pharmacologically active substances useable in the pharmaceutical composition containing compounds of formula (Ia) or (Ib) of the present invention may be selected from but are not limited to the classes consisting of B2-adrenoceptor-agonists (short and long-acting beta mimetics), anti-cholinergics (short and long-acting), anti-inflammatory steroids (oral and topical corticosteroids), dissociated-glucocorticoidmimetics, PDE3 inhibitors, PDE4 inhibitors, PDE7 inhibitors, LTD4 antagonists, EGFR inhibitors, PAF antagonists, Lipoxin A4 derivatives, FPRL1 modulators, LTB4-receptor (BLT1, BLT2) antagonists, histamine-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signaling pathway as for example IKK2 kinase inhibitors, iNOS inhibitors, MRP4 inhibitors, leukotriene biosynthesis inhibitors as for example 5-Lipoxygenase (5-LO) inhibitors, cPLA2 inhibitors, Leukotriene A4 hydrolase inhibitors or FLAP inhibitors, non-steroidal anti-inflammatory agents (NSAIDs), DP1-receptor modulators, thromboxane receptor antagonists, CCR1 antagonists, CCR2 antagonists, CCR3 antagonists, CCR4 antagonists, CCR5 antagonists, CCR6 antagonists, CCR7 antagonists, CCR8 antagonists, CCR9 antagonists, CCR10 antagonists, CXCR1 antagonists, CXCR2 antagonists, CXCR3 antagonists, CXCR4 antagonists, CXCR5 antagonists, CXCR6 antagonists, CX3CR1 antagonists, neurokinin (NK1, NK2) antagonists, sphingosine 1-phosphate receptor modulators, sphingosine 1-phosphate-lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, mucoregulators, immunotherapeutic agents, compounds against swelling of the airways, compounds against cough, CB2 agonists, retinoids, immunosuppressants, mast cell stabilizers, methylxanthine, opioid receptor agonists, laxatives, anti-foaming agents, antispasmodic agents, 5-HT4 agonists but also combinations of two or three active substances.

Preferred are combinations of two or three active substances, i.e.: CRTH2 antagonists according to the present invention with betamimetics, anticholinergics, corticosteroids, PDE4 inhibitors, LTD4 antagonists, EGFR inhibitors, CCR3 antagonists, CCR5 antagonists, CCR9 antagonists, 5-LO inhibitors, histamine receptor antagonists, SYK inhibitors and sulfonamides, or i.e.:

- CRTH2 antagonists with betamimetics and corticosteroids, PDE4 inhibitors, CCR3 antagonists or LTD4 antagonists,
- CRTH2 antagonists with anticholinergics and betamimetics, corticosteroids, PDE4 inhibitors, CCR3 antagonists or LTD4 antagonists,
- CRTH2 antagonists with corticosteroids and PDE4 inhibitors, CCR3 antagonists or LTD4 antagonists
- CRTH2 antagonists with PDE4 inhibitors and CCR3 antagonists or LTD4 antagonists In the pharmaceutical compositions according to the present invention the CRTH2 antagonists of formula (Ia) or (Ib) may be contained in a form selected from tautomers, optical isomers, enantiomers, racemates, diastereomers, pharmacologically acceptable acid addition salts, solvates or hydrates, as far as such forms exist, depending on the individual compound. Pharmaceutical compositions comprising one or more, preferably one, compound 1 in form of a substantially pure enantiomer are preferred.

In the pharmaceutical compositions according to the present invention more than one CRTH2 antagonist of formula (Ia) or (Ib) and more than one further pharmacologically active compound can be present.

Pharmaceutical Forms

Suitable preparations for administering the compounds of formula (Ia) or (Ib) include for example tablets, capsules, suppositories, solutions and powders etc. The content of the pharmaceutically active compound(s) should be in the range from 0.05 to 90 wt.-%, preferably 0.1 to 50 wt.-% of the composition as a whole.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavor enhancer, e.g. a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilizers such as alkali metal salts of ethylenediaminetetraacetic acid, optionally using emulsifiers and/or dispersants, while if water is used as diluent, for example, organic solvents may optionally be used as solubilizers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethylene glycol or the derivatives thereof.

Excipients which may be used include but are not limited to water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulfite liquors, methylcellulose, starch and polyvinylpyrrolidone) and lubricants (e.g. magnesium stearate, talc, stearic acid and sodium lauryl sulfate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulfate and talc may also be used to produce the tablets. In the case of aqueous suspensions the active substances may be combined with various flavor enhancers or colorings in addition to the above-mentioned excipients.

The compounds of formula (Ia) or (Ib) may also be administered as preparations or pharmaceutical formulations suitable for inhalation. Inhalable preparations include inhalable powders, propellant-containing metered-dose aerosols or propellant-free inhalable solutions. Within the scope of the present invention, the term propellant-free inhalable solutions also include concentrates or sterile inhalable solutions ready for use. The formulations which may be used within the scope of the present invention are described in more detail in the next part of the specification.

The inhalable powders which may be used according to the invention may contain (Ia) or (Ib) either on its own or in admixture with suitable physiologically acceptable excipients.

If the active substances (Ia) or (Ib) are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the present invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronized active substance 1, preferably with an average particle size of 0.5 to 10 µm, more preferably from 1 to 5 µm, is added to the excipient mixture. Processes for producing the inhalable powders according to the invention by grinding and micronizing and finally mixing the ingredients together are known from the prior art.

The inhalable powders according to the invention may be administered using inhalers known from the prior art.

The inhalation aerosols containing propellant gas according to the invention may contain the compounds of formula (Ia) or (Ib) dissolved in the propellant gas or in dispersed form. The compounds of formula (Ia) or (Ib) may be contained in separate formulations or in a common formulation, in which the compounds of formula (Ia) or (Ib) are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilizers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances of formula (Ia) or (Ib) according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing compounds of formula (Ia) or (Ib) are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulfuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavorings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabilizer or complexing agent may be omitted in these formulations. Other embodiments may contain this compound or these compounds. In a preferred embodiment the content based on sodium edetate is less than 100 mg/100 mL, preferably less than 50 mg/100 mL, more preferably less than 20 mg/100 mL. Generally, inhalable solutions in which the content of sodium edetate is from 0 to 10 mg/100 mL are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propylene glycol, polyethylene glycol, polypropylene glycol, glycol ether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants and/or preservatives which guarantee or prolong the shelf life of the finished pharmaceutical formulation, flavorings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 mL, more preferably between 5 and 20 mg/100 mL.

The dosage of the compounds according to the invention is naturally highly dependent on the method of administration and the complaint which is being treated. When administered by inhalation the compounds of formula (Ia) or (Ib) are characterized by a high potency even at doses in the µg range. The compounds of formula (Ia) or (Ib) may also be used effectively above the µg range. The dosage may then be in the gram range, for example.

In another aspect the present invention relates to the abovementioned pharmaceutical formulations as such which are characterized in that they contain a compound of formula (Ia) or (Ib), particularly the above-mentioned pharmaceutical formulations which can be administered by inhalation.

The following examples of formulations illustrate the present invention without restricting its scope:

Examples of pharmaceutical formulations:

| A) | Tablets | per tablet |
|---|---|---|
| | active substance (Ia) or (Ib) | 100 mg |
| | lactose | 140 mg |
| | maize starch | 240 mg |
| | polyvinylpyrrolidone | 15 mg |
| | magnesium stearate | 5 mg |
| | Σ | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) | Tablets | per tablet |
|---|---|---|
| | active substance (Ia) or (Ib) | 80 mg |
| | lactose | 55 mg |
| | maize starch | 190 mg |
| | microcrystalline cellulose | 35 mg |
| | polyvinylpyrrolidone | 15 mg |
| | sodium carboxymethyl starch | 23 mg |
| | magnesium stearate | 2 mg |
| | Σ | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance (Ia) or (Ib) | 50 mg |
| | sodium chloride | 50 mg |
| | water for inj. | 5 mL |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg and 50 mg of active substance.

| D) | Metering aerosol | |
|---|---|---|
| | active substance (Ia) or (Ib) | 0.005 |
| | sorbitan trioleate | 0.1 |
| | monofluorotrichloromethane and TG134a : TG227 2:1 | ad 100 |

The suspension is transferred into a conventional aerosol container with metering valve. Preferably 50 μl suspension are released on each actuation. The active substance may also be released in higher doses if desired (e.g. 0.02 wt.-%).

| E) | Solutions (in mg/100 mL) | |
|---|---|---|
| | active substance (Ia) or (Ib) | 333.3 mg |
| | benzalkonium chloride | 10.0 mg |
| | EDTA | 50.0 mg |
| | HCl (1N) | ad pH 2.4 |

This solution can be prepared in the usual way.

| F) | Inhalable powder | |
|---|---|---|
| | active substance (Ia) or (Ib) | 12 μg |
| | lactose monohydrate | ad 25 mg |

The inhalable powder is prepared in the usual way by mixing the individual ingredients.

The following examples serve to further illustrate the present invention without restricting its scope.

EXAMPLES

I. HPLC Methods

Method A:

HPLC-MS: Agilent 1100

Mobile phase:

A: water with 0.032% $NH_4OH$

B: methanol

| time in min | % A | % B | flow rate in mL/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |
| 2.90 | 95 | 5 | 1.50 |

Column: XBridge C18, 3.5 μm, 4.6×50 mm (column temperature: constant at 40° C.).

Detection by diode array detector at 210-500 nm wavelength.

Method B:

HPLC-MS: Waters ZQ MS, Alliance 2690/2695 HPLC, 2996 diode array detector

Mobile Phase:

A: water with 0.1% TFA

B: methanol

| time in min | % A | % B | flow rate in mL/min |
|---|---|---|---|
| 0.00 | 95 | 5 | 4.0 |
| 0.20 | 95 | 5 | 4.0 |
| 1.60 | 0 | 100 | 4.0 |
| 2.10 | 0 | 100 | 4.0 |

Column: Waters XBridge C18, 4.6×20 mm, 3.5 μm (column temperature: constant at 40° C.).

Detection by diode array detector at 210-400 nm wavelength.

Method C:
HPLC: Waters Acquity with DA and MS detector
Mobile Phase:
A: water with 0.1% TFA
B: methanol

| time in min | % A | % B | flow rate in mL/min |
|---|---|---|---|
| 0.00 | 99 | 1 | 1.5 |
| 0.05 | 99 | 1 | 1.5 |
| 1.05 | 0 | 100 | 1.5 |
| 1.20 | 0 | 100 | 1.5 |

Column: Waters XBridge BEH C18, 2.1×30 mm, 1.7 μm (column temperature: constant at 60° C.). Detection by diode array detector at 210-400 nm wavelength.
Method D:
HPLC: Waters Acquity with DA and MS detector
Mobile Phase:
A: water with 0.13% TFA
B: methanol with 0.05% TFA

| time in min | % A | % B | flow rate in mL/min |
|---|---|---|---|
| 0.00 | 99 | 1 | 1.3 |
| 0.05 | 99 | 1 | 1.3 |
| 1.05 | 0 | 100 | 1.3 |
| 1.20 | 0 | 100 | 1.3 |

Column: Waters XBridge BEH C18, 2.1×30 mm, 1.7 μm (column temperature: constant at 60° C.). Detection by diode array detector at 210-400 nm wavelength.
Method E:
HPLC: Waters Acquity with DA and MS detector
Mobile Phase:
A: water with 0.1% TFA
B: methanol

| time in min | % A | % B | flow rate in mL/min |
|---|---|---|---|
| 0.00 | 95 | 5 | 1.4 |
| 0.05 | 95 | 5 | 1.4 |
| 1.00 | 0 | 100 | 1.4 |
| 1.10 | 0 | 100 | 1.4 |

Column: Waters XBridge C18, 2.1×30 mm, 2.5 μm (column temperature: constant at 60° C.).
Detection by diode array detector at 210-400 nm wavelength.
Method F:
HPLC: Agilent 1200 with DA and MS detector
Mobile Phase:
A: water with 0.1% TFA
B: methanol

| time in min | % A | % B | flow rate in mL/min |
|---|---|---|---|
| 0.00 | 95 | 5 | 2.0 |
| 0.20 | 95 | 5 | 2.0 |
| 1.50 | 0 | 100 | 2.0 |
| 1.55 | 0 | 100 | 2.6 |
| 1.75 | 0 | 100 | 2.6 |

Column: Waters XBridge C18, 3×30 mm, 2.5 μm (column temperature: constant at 60° C.).
Detection by diode array detector at 210-400 nm wavelength.
Method G:
HPLC-MS: Waters Alliance with DA and MS detector
Mobile Phase:
A: water with 0.1% $NH_3$
B: methanol with 0.1% $NH_3$

| time in min | % A | % B | flow rate in mL/min |
|---|---|---|---|
| 0.00 | 95 | 5 | 4.0 |
| 0.20 | 95 | 5 | 4.0 |
| 1.50 | 0 | 100 | 4.0 |
| 1.75 | 0 | 100 | 4.0 |

Column: Waters XBridge C18, 4.6×30 mm, 3.5 μm (column temperature: constant at 60° C.).
Detection by diode array detector at 210-400 nm wavelength.
Method H:
HPLC-MS: Waters Alliance with DA and MS detector
Mobile Phase:
A: water with 0.1% TFA
B: methanol

| time in min | % A | % B | flow rate in mL/min |
|---|---|---|---|
| 0.00 | 95 | 5 | 4.8 |
| 1.60 | 0 | 100 | 4.8 |
| 1.85 | 0 | 100 | 4.8 |
| 1.90 | 95 | 5 | 4.8 |

Column: Waters SunFire C18, 4.6×30 mm, 3.5 μm (column temperature: constant at 60° C.).
Detection by diode array detector at 210-400 nm wavelength.
Method J:
HPLC: Waters Acquity with DA and MS detector
Mobile Phase:
A: water with 0.13% TFA
B: methanol with 0.05% TFA

| time in min | % A | % B | flow rate in mL/min |
|---|---|---|---|
| 0.00 | 99 | 1 | 1.2 |
| 0.15 | 99 | 1 | 1.2 |
| 1.10 | 0 | 100 | 1.2 |
| 1.25 | 0 | 100 | 1.2 |

Column: Waters Sunfire C18, 2.1×30 mm, 2.5 μm (column temperature: constant at 60° C.).
Detection by diode array detector at 210-400 nm wavelength.
Method K:
HPLC-MS: Waters Alliance with DA and MS detector
Mobile Phase:
A: water with 0.1% TFA
B: methanol with 0.1% TFA

| time in min | % A | % B | flow rate in mL/min |
|---|---|---|---|
| 0.00 | 95 | 5 | 4.0 |
| 0.20 | 95 | 5 | 4.0 |
| 1.50 | 0 | 100 | 4.0 |

| time in min | % A | % B | flow rate in mL/min |
| --- | --- | --- | --- |
| 1.75 | 0 | 100 | 4.0 |
| 1.85 | 95 | 5 | 4.0 |

Column: Waters XBridge C18, 4.6×30 mm, 3.5 μm (column temperature: constant at 60° C.).
Detection by diode array detector at 210-400 nm wavelength.
Method L:
HPLC-MS: Waters Alliance with DA and MS detector
Mobile Phase:
A: water with 0.1% TFA
B: methanol

| time in min | % A | % B | flow rate in mL/min |
| --- | --- | --- | --- |
| 0.00 | 95 | 5 | 4.8 |
| 1.60 | 0 | 100 | 4.8 |
| 1.85 | 0 | 100 | 4.8 |
| 1.90 | 95 | 5 | 4.8 |

Column: Waters XBridge C18, 4.6×30 mm, 3.5 μm (column temperature: constant at 60° C.).
Detection by diode array detector at 210-400 nm wavelength.
Method M:
HPLC-MS: Waters 2695 HPLC, ZQ MS, 2996 diode array detector, 2695 autosampler
Mobile Phase:
A: water with 0.1% $NH_3$
B: methanol with 0.1% $NH_3$

| time in min | % A | % B | flow rate in mL/min |
| --- | --- | --- | --- |
| 0.00 | 95 | 5 | 4.0 |
| 0.20 | 95 | 5 | 4.0 |
| 1.50 | 0 | 100 | 4.0 |
| 1.75 | 0 | 100 | 4.0 |

Column: Waters XBridge C18, 4.6×30 mm, 3.5 μm (column temperature: constant at 60° C.).
Detection by diode array detector at 210-400 nm wavelength.
Method N:
HPLC: Waters Acquity with DA and MS detector
Mobile Phase:
A: water with 0.13% TFA
B: methanol with 0.08% TFA

| time in min | % A | % B | flow rate in mL/min |
| --- | --- | --- | --- |
| 0.00 | 99 | 1 | 1.3 |
| 0.05 | 99 | 1 | 1.3 |
| 0.35 | 0 | 100 | 1.3 |
| 0.50 | 0 | 100 | 1.3 |

Column: Waters XBridge BEH C18, 2.1×30 mm, 1.7 μm (column temperature: constant at 60° C.). Detection by diode array detector at 210-400 nm wavelength.
Method O:
HPLC: Agilent 1200 with DA and MS detector
Mobile Phase:
A: water with 0.1% TFA
B: methanol

| time in min | % A | % B | flow rate in mL/min |
| --- | --- | --- | --- |
| 0.00 | 95 | 5 | 1.9 |
| 0.20 | 95 | 5 | 1.9 |
| 1.55 | 0 | 100 | 1.9 |
| 1.60 | 0 | 100 | 2.4 |
| 1.80 | 0 | 100 | 2.4 |

Column: Waters XBridge C18, 3×30 mm, 2.5 μm (column temperature: constant at 60° C.).
Detection by diode array detector at 210-400 nm wavelength.

II. Synthesis of Starting Compounds

A) Synthesis of Amines

1.) [1-(4-Aminobenzyl)-3,5-dimethyl-1H-pyrazol-4-yl]acetic acid methyl ester a) To a solution of (3,5-dimethyl-1H-pyrazol-4-yl)acetic acid methyl ester (3.90 g, 23 mmol) and 4-nitrobenzyl bromide (4.60 g, 20.7 mmol) in acetonitrile is added $K_2CO_3$ (2.76 g, 19.9 mmol) and the mixture is stirred for one hour at room temperature. The reaction mixture is poured into water and extracted twice with ethyl acetate. The organic phase is dried over $MgSO_4$ and evaporated under reduced pressure. To yield 7.50 g of [3,5-Dimethyl-1-(4-nitro-benzyl)-1H-pyrazol-4-yl]-acetic acid methyl ester (ESI mass spectrum: $[M+H]^+$=304).

b) To a solution of [3,5-dimethyl-1-(4-nitrobenzyl)-1H-pyrazol-4-yl]acetic acid methyl ester (3.90 g, 10.3 mmol) in methanol (10 mL) is added 10% palladium on charcoal (500 mg) and the mixture is hydrogenated. The catalyst is filtered off and the filtrate is concentrated under reduced pressure. The mixture is purified via preparative reversed phase HPLC (gradient of methanol in water+0.1% $NH_3$) to yield 1.18 g of the title compound (ESI mass spectrum: $[M+H]^+$=274; Retention time HPLC: 2.13 min (method A))

2.) [1-(4-Amino-2-chloro-benzyl)-3,5-dimethyl-1H-pyrazol-4-yl]acetic acid ethyl ester a) To a solution of (3,5-dimethyl-1H-pyrazol-4-yl)acetic acid ethyl ester (1.40 g, 7.7 mmol) and 2-chloro-4-nitrobenzyl bromide (4.60 g, 20.7 mmol) in 20 mL acetonitrile is added $K_2CO_3$ (1.59 g, 11.5 mmol) and the mixture is stirred for 48 hours at room temperature. The solvent is removed by evaporation and the residue is dissolved in dichloromethane/water. After extraction with dichloromethane the organic layer is dried over $Na_2SO_4$ and evaporated under reduced pressure to yield 2.79 g of [3,5-dimethyl-1-(2-chloro-4-nitro-benzyl)-1H-pyrazol-4-yl]-acetic acid ethyl ester (ESI mass spectrum: $[M+H]^+$=352; Retention time: 1.95 min (method A).

b) To a solution [3,5-dimethyl-1-(2-chloro-4-nitrobenzyl)-1H-pyrazol-4-yl]acetic acid ethyl ester (2.39 g, 6.8 mmol) in methanol (40 mL) is added Raney nickel (250 mg) and the mixture is hydrogenated. The catalyst is filtered off and the filtrate is concentrated under reduced pressure to yield 1.18 g of the title compound (ESI mass spectrum: $[M+H]^+$=322; Retention time HPLC: 1.76 min (method A)).

3.) [1-(4-Amino-benzyl)-3,5-diethyl-1H-pyrazol-4-yl]acetic acid ethyl ester a) To a solution of (3,5-diethyl-1H-pyrazol-4-yl) acetic acid ethyl ester (10.95 g, 52.1 mmol) and 4-nitrobenzyl bromide (14.625 g, 68 mmol) in acetonitrile (110 mL) is added $K_2CO_3$ (10.80 g, 78.1 mmol) and the mixture is stirred for 48 hours at room temperature. The reaction mixture is poured into water and extracted twice with ethyl acetate. The organic phase is dried over $MgSO_4$ and evaporated under reduced pressure. The residue is purified by MPLC with ethyl acetate/cyclohexane to yield 12.50 g [3,5-diethyl-1-(4-nitro-benzyl)-1H-pyrazol-4-yl]acetic acid ethyl ester (ESI mass spectrum: $[M+H]^+$=346; Retention time HPLC: 1.42 min (method B)).
b) To a solution of [3,5-diethyl-1-(4-nitro-benzyl)-1H-pyrazol-4-yl]acetic acid ethyl ester (6.66 g, 19.3 mmol) in methanol (500 mL) is added Raney nickel (500 mg) and the mixture is hydrogenated at 50 psi and room temperature. The catalyst is filtered off and the filtrate is concentrated under reduced pressure to yield 4.38 g of the title compound (ESI mass spectrum: $[M+H]^+$=316; Retention time HPLC: 1.09 min (method B)).

4.) [1-(4-Amino-2-fluorobenzyl)-3,5-dimethyl-1H-pyrazol-4-yl]acetic acid methyl ester a) To a solution of (3,5-dimethyl-1H-pyrazol-4-yl)-acetic acid methyl ester (10 g, 48.9 mmol) and 2-fluoro-4-nitrobenzyl bromide (11.5 g, 49.1 mmol) in acetonitrile (150 mL) is added $K_2CO_3$ (10.1 g, 73.3 mmol) and the mixture is stirred for 48 hours at 60° C. The solvent is removed by evaporation and the residue is dissolved in dichloromethane/water. After extraction with dichloromethane the organic layer is dried over $Na_2SO_4$ and evaporated under reduced pressure. The residue is purified by MPLC (cyclohexane/diethyl ether 7:3) to yield 13 g of [3,5-dimethyl-1-(2-fluoro-4-nitrobenzyl)-1H-pyrazol-4-yl]acetic acid methyl ester (ESI mass spectrum: $[M+H]^+$=322; Retention time (HPLC): 0.85 min (method C)).
b) To a solution of [3,5-dimethyl-1-(2-fluoro-4-nitro-benzyl)-1H-pyrazol-4-yl]acetic acid methyl ester (13 g, 40.4 mmol) in methanol (250 mL) is added Raney nickel (6 g) and the mixture is hydrogenated at 50 psi and 50° C. The catalyst is filtered off and the filtrate is concentrated under reduced pressure. The mixture is purified by crystallization in diisopropyl ether to yield 12.8 g of the title compound (ESI mass spectrum: $[M+H]^+$=292; Retention time HPLC: 0.61 min (method C)).

5.) [1-(4-Amino-2-chloro-benzyl)-3,5-dimethyl-1H-pyrazol-4-yl]-acetic acid tert-butyl ester a) To a solution of (3,5-dimethyl-1H-pyrazol-4-yl)-acetic acid tert-butyl ester (2.6 g, 12.4 mmol, preparation according to WO2007/141267 by using 2,4-pentanedione instead of 3,5-heptanedione) and 2-chloro-4-nitrobenzyl bromide (3.11 g, 12.4 mmol) in acetonitrile (30 mL) is added $K_2CO_3$ (2.575 g, 18.6 mmol) and the mixture is stirred for 48 hours at room temperature and after that 2 hours at 60° C. The solid is filtered off and the solvent is removed by evaporation. The residue is dissolved in dichloromethane/water. After extraction with dichloromethane the organic layer is dried over $MgSO_4$ and evaporated under reduced pressure to yield 4.4 g of [3,5-dimethyl-1-(2-chloro-4-nitrobenzyl)-1H-pyrazol-4-yl]acetic acid tert-butyl ester (ESI mass spectrum: $[M+H]^+$=380).
b) To a solution of [3,5-dimethyl-1-(2-chloro-4-nitrobenzyl)-1H-pyrazol-4-yl]acetic acid tert-butyl ester (4.40 g, 11.6 mmol) in methanol (80 mL) is added Raney nickel (440 mg) and the mixture is hydrogenated at 50 psi and room temperature for 12 hours. The catalyst is filtered off and the filtrate is concentrated under reduced pressure to yield 2.4 g of the title compound (ESI mass spectrum: $[M+H]^+$=350; Retention time HPLC: 0.76 min (method D)).

6.) [1-(4-Aminobenzyl)-3,5-dimethyl-1H-pyrazol-4-yl]acetic acid tert-butyl ester The title compound (ESI mass spectrum: $[M+H]^+$=316; Retention time HPLC: 0.65 min (method E)) is synthesized in analogy to procedure II.A.5 by using 4-nitrobenzylbromide instead of 2-fluoro-4-nitrobenzylbromide.

7.) [1-(4-Amino-2-fluorobenzyl)-3,5-dimethyl-1H-pyrazol-4-yl]acetic acid tert-butyl ester a) To a solution of (3,5-dimethyl-1H-pyrazol-4-yl)acetic acid tert-butyl ester (10 g, 47.6 mmol, preparation according to WO2007/141267 by using 2,4-pentanedione instead of 3,5-heptanedione) and 2-fluoro-4-nitrobenzyl bromide (11.2 g, 47.9 mmol) in acetonitrile (150 mL) is added $K_2CO_3$ (6.615 g, 47.9 mmol) and the mixture is stirred for 24 hours at room temperature. The solid is filtered off and the solvent is removed by evaporation. The residue is dissolved in dichloromethane/water. After extraction with dichloromethane the organic layer is dried over $MgSO_4$ and evaporated under reduced pressure. The residue is purified by MPLC (cyclohexane/ethyl acetate 7:3, silicagel 60) to yield 13.6 g of [3,5-dimethyl-1-(2-fluoro-4-nitrobenzyl)-1H-pyrazol-4-yl]acetic acid tert-butyl ester (ESI mass spectrum: $[M+H]^+$=364 TLC: Rf=0.23 (cyclohexan/ethyl acetate 7:3, solicagel 60 F254)).
b) To a solution of [3,5-dimethyl-1-(2-fluoro-4-nitrobenzyl)-1H-pyrazol-4-yl]acetic acid tert-butyl ester (13.6 g, 37.4 mmol) in methanol (250 mL) is added Raney nickel (6 g) and the mixture is hydrogenated at 50 psi and 50° C. for 12 hours. The catalyst is filtered off and the filtrate is concentrated under reduced pressure to yield 11.6 g of the title compound (ESI mass spectrum: $[M+H]^+$=334; TLC: Rf=0.53 (dichloromethane/methanol 95:5, silicagel 60 F254)).

B) Synthesis of carboxylic acids

1.) 1-Ethyl-5-fluoro-1H-indole-2-carboxylic acid a) To a solution of 5-fluoroindol-2-ethyl ester (200 mg, 0.965 mmol) in dimethylsulfoxide (6 mL) is added potassium tert-butylate (108 mg, 0.965 mmol) and the mixture is stirred at 50° C. for 30 minutes. After cooling to room temperature bromoethane (0.081 mL, 1.06 mmol) is added and the mixture is stirred at room temperature for 2.5 hours. With cooling water is added and the mixture is extracted with ethyl acetate. The organic layer is washed with water and saturated aqueous NaCl solution, dried over $MgSO_4$ and the solvent is evaporated in vacuo to yield 200 mg of 1-ethyl-5-fluoro-1H-indole-2-carboxylic acid ethyl ether (ESI mass spectrum: $[M+H]^+$=236).
b) To a solution of 1-ethyl-5-fluoro-1H-indole-2-carboxylic acid ethyl ether (200 mg, 0.85 mmol) in dioxane (2 mL) is added an aqueous solution of NaOH (1 M, 1.7 mL) and the mixture is stirred at 60° C. for 1 hour. After evaporation of the solvent the residue was suspended in a few water and neutralized with acetic acid (2 M). The precipitate is filtered, washed with water and dried to yield 140 mg of the title compound (ESI mass spectrum: $[M+H]^+$=208; Retention time HPLC: 1.21 min (method F)).

The following indole carboxylic acids are prepared likewise in analogy to this method:

1-Benzyl-1H-indole-2-carboxylic acid (ESI mass spectrum: [M+H]$^+$=252 Retention time HPLC: 0.84 min (method E));

1-Butyl-1H-indole-2-carboxylic acid (ESI mass spectrum: [M+H]$^+$=218);

5-Fluoro-1-propyl-1H-indole-2-carboxylic acid (ESI mass spectrum: [M+H]$^+$=222);

1-Butyl-5-fluoro-1H-indole-2-carboxylic acid (ESI mass spectrum: [M+H]$^+$=236);

1-Propyl-1H-indole-2-carboxylic acid (ESI mass spectrum: [M+H]$^+$=204);

1-Ethyl-4-fluoro-1H-indole-2-carboxylic acid (ESI mass spectrum: [M+H]$^+$=208; Retention time HPLC: 0.80 min (method E);

1-Ethyl-6-fluoro-1H-indole-2-carboxylic acid (ESI mass spectrum: [M+H]$^-$=206; Retention time HPLC: 0.71 min (method E));

6-Fluoro-1-propyl-1H-indole-2-carboxylic acid (ESI mass spectrum: [M–H]$^-$=220; Retention time HPLC: 0.77 min (method E)).

2.) 3-Ethyl-5-fluorobenzofuran-2-carboxylic acid a) To a solution of 5-fluoro-2-hydroxy-propiophenone (0.9 g, 5.2 mmol) and tert-butyl bromoacetate (0.9 mL, 6.1 mmol) in acetonitrile (15 mL) is added K$_2$CO$_3$ (1.08 g, 7.8 mmol) and the mixture is refluxed for 3 hours. After cooling to room temperature the mixture is poured into water and extracted with ethyl acetate. The organic layer is washed twice with water, dried over MgSO$_4$ and the solvent is evaporated in vacuo to yield 1.47 g of (4-fluoro-2-propionylphenoxy)acetic acid tert-butyl ester (ESI mass spectrum: [M+H]$^+$=283; Retention time HPLC: 0.88 min (method D)).

b) To a solution of (4-fluoro-2-propionylphenoxy)acetic acid tert-butyl ester (1.47 g, 5.2 mmol) in dry ethanol (20 mL) is added solution of sodium methanolate in methanol (5.4 M, 20 mL) and the mixture is stirred at 80° C. for 12 hours. After cooling to room temperature and evaporation of the solvent the residue was dissolved in water and acidified with hydrochloric acid (1 M). The precipitate is filtered, washed with water and dried to yield 440 mg of the title compound (ESI mass spectrum: [M–H]$^-$=207; Retention time HPLC: 0.87 min (method G)).

The following benzofuran carboxylic acids are prepared likewise in analogy to this method:

7-Chloro-3-methylbenzofuran-2-carboxylic acid (ESI mass spectrum: [M–H]$^-$=209; Retention time HPLC: 1.28 min (method H));

5-Fluoro-3-propylbenzofuran-2-carboxylic acid (ESI mass spectrum: [M–H]$^-$=221; Retention time HPLC: 1.01 min (method G));

3-Ethyl-7-fluorobenzofuran-2-carboxylic acid (ESI mass spectrum: [M–H]$^-$=207; Retention time HPLC: 0.77 min (method E));

3-Ethyl-5,7-difluorobenzofuran-2-carboxylic acid (ESI mass spectrum: [M–H]$^-$=225; Retention time HPLC: 1.32 min (method L));

6-Chlorobenzofuran-2-carboxylic acid (ESI mass spectrum: [M–H]$^-$=195; Retention time HPLC: 1.72 min (method H)).

III) Synthesis of Compounds (Ia) and (Ib)

Compound 1: (1-(2-fluoro-4-[(1H-indole-2-carbonyl)amino]benzyl)-3,5-dimethyl-1H-pyrazol-4-yl)acetic acid (Coupling method C1)

a) To a solution of indole-2-carboxylic acid (80 mg, 0.50 mmol) in N,N-dimethylformamide (1.5 mL) are added TBTU (139 mg, 0.43 mmol) and N,N-diisopropyl amine (0.126 mL, 0.74 mmol). Subsequently [1-(4-amino-2-fluorobenzyl)-3,5-dimethyl-1H-pyrazol-4-yl]acetic acid methyl ester (120 mg, 0.41 mmol) is added. The mixture is stirred at room temperature for 12 hours. After that an aqueous solution of K$_2$CO$_3$ (2 M, 0.5 mL) is added. The obtained mixture is flushed through Al$_2$O$_3$ with dichloromethane/methanol (9:1, 10 mL). The solvent is removed in vacuo to yield 82.3 mg of (1-(2-fluoro-4-[(1H-indole-2-carbonyl)amino]benzyl)-3,5-dimethyl-1H-pyrazol-4-yl)acetic acid methyl ester (ESI mass spectrum: [M+H]$^+$=435; Retention time HPLC: 0.41 min (method N).

b) (1-(2-Fluoro-4-[(1H-indole-2-carbonyl)amino]benzyl)-3,5-dimethyl-1H-pyrazol-4-yl)acetic acid methyl ester (82 mg, 0.19 mmol) is dissolved in methanol (0.5 mL). An aqueous solution of NaOH (4M, 0.3 mL) is added and the mixture is stirred at room temperature for 2 hours. The resulting mixture is diluted with methanol/water, the solid is filtered off and after evaporation the residue is purified by HPLC (Gilson, XRS Pursuit, methanol/H$_2$O+0.1% conc. NH$_3$). The fractions containing the title compound are concentrated and lyophilized to yield 15 mg of the title compound (ESI mass spectrum: [M+H]$^+$=421; Retention time HPLC: 1.04 min (method G)).

$^1$H-NMR 400 MHz (DMSO-d6): δ [ppm]=2.03 (s, 3H), 2.14 (s, 3H), 2.52 (s, 3H), 3.21 (s, 2H), 5.16 (s, 2H), 6.99 (t, 1H), 7.08 (t, 1H), 7.23 (t, 1H), 7.39 (s, 1H), 7.48 (m, 2H), 7.66 (d, 1H), 7.79 (d, 1H), 10.45 (s, 1H), 11.79 (br., 1H).

Compounds 2 and 3 of table 1 below have likewise been prepared in analogy to coupling method C1 using suitable starting amines and carboxylic acids.

Compound 4: (1-{4-[(5-Fluoro-3-methylbenzofuran-2-carbonyl)amino]benzyl}-3,5-dimethyl-1H-pyrazol-4-yl) acetic acid (Coupling method C2)

a) To a solution of [1-(4-aminobenzyl)-3,5-dimethyl-1H-pyrazol-4-yl]acetic acid methyl ester (400 mg, 1.46 mmol) in 5 mL dichloromethane are added diisopropylethylamine (1.5 mL, 8.8 mmol) and 5-fluoro-3-methyl-1-benzofuran-2-carboxylic acid (369 mg, 1.9 mmol). After stiffing at room temperature for 10 minutes a 50% solution of 1-propylphosphonic acid cyclic anhydride in ethyl acetate (1.725 mL, 2.93 mmol) is added with cooling and the mixture is stirred at room temperature for 12 hours. The solvent is evaporated in vacuo and the residue is purified by MPLC (dichloromethane/methanol 98:2) to yield 410 mg of (1-{4-[(5-fluoro-3-methylbenzofuran-2-carbonyl)amino]benzyl}-3,5-dimethyl-1H-pyrazol-4-yl)acetic acid methyl ester (ESI mass spectrum: [M+H]$^+$=450; TLC: Rf=0.56 (dichloromethane/methanol 95:5, silicagel 60 F254)).

b) To a solution of (1-{4-[(5-fluoro-3-methylbenzofuran-2-carbonyl)amino]benzyl}-3,5-dimethyl-1H-pyrazol-4-yl) acetic acid methyl ester (410 mg, 0.91 mmol) in dioxane/water (10 mL/10 mL) is added 1 M NaOH (2.3 mL) and the mixture is stirred at room temperature for 24 hours. The mixture is diluted with water and acidified with hydrochloric acid (1 M, 3.25 mL). The precipitate is filtered, washed with water and dried to yield 338 mg of the title compound (ESI mass spectrum: [M+H]$^+$=436; Retention time HPLC: 0.85 min (method D).

¹H-NMR 400 MHz (DMSO-d6): δ [ppm]=2.05 (s, 3H), 2.10 (s, 3H), 2.52 (s, 3H), 3.24 (s, 2H), 5.16 (s, 2H), 7.10 (d, 2H), 7.37 (t, 1H), 7.66 (m, 2H), 7.75 (d, 2H), 10.40 (s, 1H), 12.05 (br., 1H).

Compounds 5 to 26 and 57 to 59 of tables 1 and 2 below have likewise been prepared in analogy to coupling method C2 using suitable starting amines and carboxylic acids.

Compound 27: (1-{2-Fluoro-4-[(5-fluoro-3-methylbenzofuran-2-carbonyl)amino]benzyl}-3,5-dimethyl-1H-pyrazol-4-yl)acetic acid (Coupling method C3):
a) To a solution of 5-fluoro-3-methyl-1-benzofuran-2-carboxylic acid (194 mg, 1 mmol) in 5 mL dimethylformamide is added diisopropylethylamine (0.516 mL, 3 mmol) and HATU (399 mg, 1.05 mmol) is added. After stirring at room temperature for 25 minutes dimethylformamide (1 mL) and then intermediate [1-(4-amino-2-fluorobenzyl)-3,5-dimethyl-1H-pyrazol-4-yl]acetic acid methyl ester (291 mg, 1 mmol) is added. Subsequently diisopropylethylamine (0.344 mL, 2 mmol) and dimethylformamide (2 mL) is added, and the mixture is stirred at room temperature for 48 hours. Then ethyl acetate and water are added and the precipitate is filtered off. The organic layer is extracted twice with acetic acid (1 N), once with an aqueous solution of NaHCO₃ (5% by weight) and twice with water, dried over MgSO₄. The solvent is removed by evaporation in vacuo. The residue is purified by MPLC (dichloromethane/methanol 96:4) to yield 120 mg of (1-(2-fluoro-4-[(5-fluoro-3-methylbenzofuran-2-carbonyl)amino]benzyl)-3,5-dimethyl-1H-pyrazol-4-yl)acetic acid methyl ester (ESI mass spectrum: [M+H]⁺=468; TLC: Rf=0.72 (dichloromethane/methanol 9:1, silicagel 60 F254)).
b) To a solution of (1-(2-fluoro-4-[(5-fluoro-3-methylbenzofuran-2-carbonyl)-amino]-benzyl)-3,5-dimethyl-1H-pyrazol-4-yl)-acetic acid methyl ester (119 mg, 0.26 mmol) in dioxane/water (7 mL/7 mL) is added an aqueous solution of NaOH (1 M, 2.3 mL) and the mixture is stirred at room temperature for 12 hours and at 60° C. for 2 hours. The mixture is diluted with water, acidified with hydrochloric acid (1 M, 1 mL) and extracted with ethyl acetate. The organic layer is dried over MgSO₄, the solvent evaporated in vacuo, the residue is crystallized with diisopropyl ether and the precipitate is isolated by filtration to yield 69 mg of the title compound (ESI mass spectrum: [M+H]⁺=454; Retention time HPLC: 0.90 min (method D)).
¹H-NMR 400 MHz (DMSO-d6): δ [ppm]=2.03 (s, 3H), 2.14 (s, 3H), 2.57 (s, 3H), 3.28 (s, 2H), 5.18 (s, 2H), 6.96 (t, 1H), 7.37 (t, 1H), 7.54 (d, 1H), 7.66 (m, 2H), 7.79 (d, 1H), 10.60 (s, 1H), 12.07 (br., 1H).

Compounds 28 to 31 of table 1 below have likewise been prepared in analogy to coupling method C3 using suitable starting amines and carboxylic acids.

Compounds 32: (1-(4-[(1-Ethyl-5-fluoro-1H-indole-2-carbonyl)amino]-2-fluorobenzyl)-3,5-dimethyl-1H-pyrazol-4-yl)acetic acid (Coupling method C4)
a) To a solution of 1-ethyl-5-fluoro-1H-indole-2-carboxylic acid (140 mg, 0.68 mmol) in 6 mL dichloromethane is added oxalyl chloride (0.094 mL, 0.68 mmol) and a drop dimethylformamide. After stirring at room temperature for 1 hour the solvent is removed by evaporation in vacuo. The residue is dissolved in dichloromethane (5 mL) and dropped to a solution of [1-(4-amino-2-fluorobenzyl)-3,5-dimethyl-1H-pyrazol-4-yl]acetic acid methyl ester (177 mg, 0.61 mmol) and diisopropylethylamine (0.23 mL, 1.35 mmol) in dichloromethane (5 mL). After addition of 4-dimethylaminopyridine (8.255 mg, 0.069 mmol) the solution is stirred at room temperature for 12 hours. The solution is extracted twice with hydrochloric acid (1 M), twice with water, twice with an aqueous solution of NaOH (1 M) and twice with water. The organic layer is dried over MgSO₄, filtered and the solvent is evaporated in vacuo. The residue is purified by MPLC (dichloromethane/methanol 95:5) to yield 160 mg of (1-(4-[(1-ethyl-5-fluoro-1H-indole-2-carbonyl)amino]-2-fluorobenzyl)-3,5-dimethyl-1H-pyrazol-4-yl)acetic acid methyl ester (ESI mass spectrum: [M+H]⁺=481; Retention time HPLC: 0.93 min (method D)).
b) To a solution of (1-(4-[(1-ethyl-5-fluoro-1H-indole-2-carbonyl)amino]-2-fluorobenzyl)-3,5-dimethyl-1H-pyrazol-4-yl)acetic acid methyl ester (160 mg, 0.33 mmol) in dioxane (2 mL) is added an aqueous solution of NaOH (1 M, 0.66 mL) and the mixture is stirred at 60° C. for 1 hour. The solvent is evaporated in vacuo, and the residue is suspended in water and treated with acetic acid (2 M). The precipitate is freeze dried, dissolved in methanol and a little dimethylformamide, and the product is precipitated with a little water, filtered and dried to yield 137 mg of the title compound (ESI mass spectrum: [M+H]⁺=467; Retention time HPLC: 0.89 min (method D)).
¹H-NMR 400 MHz (DMSO-d6): δ [ppm]=1.30 (t, 6H), 2.04 (s, 3H), 2.13 (s, 3H), 3.25 (s, 2H), 4.55 (q, 4H), 5.16 (s, 2H), 6.97 (t, 1H), 7.17 (t, 1H), 7.29 (s, 1H), 7.47 (m, 1H), 7.62 (dd, 1H), 7.74 (d, 1H), 10.52 (s, 1H).

Compound 33: (1-(4-[(7-Chloro-3-methylbenzofuran-2-carbonyl)amino]benzyl)-3,5-dimethyl-1H-pyrazol-4-yl)acetic acid (Coupling method C4):
a) To a solution of 7-chloro-3-methylbenzofuran-2-carboxylic acid (185 mg, 0.88 mmol) in 6 mL dichloromethane is added oxalyl chloride (0.123 mL, 1.14 mmol) and a drop of dimethylformamide. After stirring at room temperature for 1 hour the solvent is removed by evaporation in vacuo. The residue is dissolved in dichloromethane (5 mL) and dropped to a solution of [1-(4-aminobenzyl)-3,5-dimethyl-1H-pyrazol-4-yl]acetic acid tert-butyl ester (428 mg, 1 mmol) in form of the toluene sulfonate salt and diisopropylethylamine (0.39 mL, 2.27 mmol) in dichloromethane (5 mL). After addition of 4-dimethylaminopyridine (11 mg, 0.09 mmol) the solution is stirred at room temperature for 12 hours. The solution is extracted twice with hydrochloric acid (1 M), twice with water, twice with an aqueous solution of NaOH (1 M) and twice with water. The organic layer is dried over MgSO₄, filtered and the solvent is evaporated in vacuo to yield 426 mg of (1-(4-[(7-chloro-3-methyl-benzofuran-2-carbonyl)amino]benzyl)-3,5-dimethyl-1H-pyrazol-4-yl)acetic acid tert-butyl ester (ESI mass spectrum: [M+H]⁺=508; Retention time HPLC: 1.60 min (method H)).
b) To a solution of (1-(4-[(7-chloro-3-methyl-benzofuran-2-carbonyl)amino]benzyl)-3,5-dimethyl-1H-pyrazol-4-yl)acetic acid tert-butyl ester (426 mg, 0.84 mmol) in dichloromethane (10 mL) is added trifluoroacetic acid (400 mL, 5.2 mmol) and the mixture is stirred at room temperature for 3 days. The solvent is evaporated in vacuo, and the residue is suspended in water and treated with diethyl ether and the precipitating product is filtered off to yield 174 mg of the title compound (ESI mass spectrum: [M+H]⁺=452; Retention time HPLC: 1.39 min (method J)).
¹H-NMR 400 MHz (DMSO-d6): δ [ppm]=2.07 (s, 3H), 2.14 (s, 3H), 2.57 (s, 3H), 3.29 (s, 2H), 5.17 (s, 2H), 7.12 (d, 2H), 7.38 (t, 1H), 7.62 (d, 1H), 7.74 (d, 2H), 7.76 (d, 1H), 10.33 (s, 1H).

Compound 48: (1-(4-[(3-Ethyl-5-fluorobenzofuran-2-carbonyl)amino]benzyl)-3,5-dimethyl-1H-pyrazol-4-yl)-acetic acid (Coupling method C4)
a) To a solution of 3-ethyl-5-fluorobenzofuran-2-carboxylic acid (450 mg, 2.16 mmol) in 10 mL dichloromethane is added oxalyl chloride (0.335 mL, 3.1 mmol) and a drop dimethylformamide. After stirring at room temperature for 1 hour the solvent is removed by evaporation in vacuo. The residue is dissolved in dichloromethane (10 mL) and dropped to a solution of [1-(4-aminobenzyl)-3,5-dimethyl-1H-pyrazol-4-yl]acetic acid tert-butyl ester (1.054 g, 2.16 mmol) in the form of the 4-toluenesulphonate salt and diisopropylethylamine (1.3 mL, 7.57 mmol) in dichloromethane (5 mL). After addition of 4-dimethylaminopyridine (26.4 mg, 0.216 mmol) the solution is stirred at room temperature for 12 hours. The solvent is evaporated in vacuo, dissolved in 100 mL ethyl acetate, and the solution is extracted twice with water, once with hydrochloric acid (0.5 M), once with water, once with an aqueous solution of $NaHCO_3$ (5% by weight) and once with water. The organic layer is dried over $MgSO_4$, filtered and the solvent is evaporated in vacuo. The residue is purified by MPLC (dichloromethane/methanol 98:2) to yield 150 mg of 1-(4-[(3-ethyl-5-fluorobenzofuran-2-carbonyl)amino]benzyl)-3,5-dimethyl-1H-pyrazol-4-yl)-acetic acid tert-butyl ester (ESI mass spectrum: $[M+H]^+$=506; Retention time HPLC: 1.02 min (method D)).

b) To a solution of 1-(4-[(3-ethyl-5-fluorobenzofuran-2-carbonyl)amino]benzyl)-3,5-dimethyl-1H-pyrazol-4-yl)-acetic acid tert-butyl ester (150 mg, 0.30 mmol) in acetonitrile (25 mL) is added montmorillonite KSF (300 mg) and the mixture is refluxed for 6 hours. The mixture is diluted to 400 mL with acetonitrile, refluxed for 5 minutes and filtered. The solvent is evaporated in vacuo and the residue is washed with dimethylformamide (300 mL).

After filtration the solvent is removed by evaporation and the residue is treated with acetone (200 mL). After trituration, the precipitate is filtered off and washed with acetone to yield 112 mg of the title compound (ESI mass spectrum: $[M+H]^+$=450; Retention time HPLC: 0.85 min (method E)).

$^1$H-NMR 400 MHz (DMSO-d6): δ [ppm]=1.21 (t, 6H), 2.04 (s, 3H), 2.11 (s, 3H), 3.09 (q, 4H), 3.27 (s, 2H), 5.16 (s, 2H), 7.09 (d, 2H), 7.33 (t, 1H), 7.67 (m, 2H), 7.76 (d, 2H), 10.39 (s, 1H).

Compounds 34 to 47 and 49 to 56 of table 1 below have likewise been prepared in analogy to coupling method C4 using suitable starting amines and carboxylic acids.

IV) Biological Assays

The compounds of formula (Ia) and (Ib) according to the invention were tested using the following biological test methods to determine their ability to displace $PGD_2$ from the CRTH2 receptor and for their ability to antagonize the functional effects of $PGD_2$ at the CRTH2 receptor in a whole system.

Preparation of Human CRTH2 Receptor Membranes and Radioligand Binding Assay

The binding of CRTH2 antagonists is determined using membranes prepared from Chinese hamster ovary cells (CHO-K1 cells) transfected with the human CRTH2 receptor (CHO-K1-hCRTH2 cells, Perkin Elmer, Cat No ES-561-C). To produce cell membranes the CHO-K1-hCRTH2 cells are cultured in suspension in CHO SFMII medium supplemented with 400 μg/mL G418. The cells are harvested by centrifugation at 300 g for 10 min at room temperature. The cell pellet is resuspended in Phosphate Buffer Saline (PBS) including a protease inhibitor mix (Complete, Roche) and adjusted to a concentration of 10E7 cells/mL. The CHO-K1-hCRTH2 cells are disrupted by nitrogen decomposition to obtain the membrane preparation. Cell debris is removed by centrifugation (500 g at 4° C., 30 min) and the supernatant is transferred into fresh tubes followed by a second centrifugation at 40000 g for 1 hour at 4° C. to sediment the membranes. The membranes are suspended in SPA incubation buffer (50 mM Tris HCl, 10 mM $MgCl_2$, 150 mM NaCl, 1 mM EDTA, pH 7.4) without bovine serum albumin, homogenized by passing through a single use needle (Terumo, 23G×1"), and stored in aliquots at −80° C.

The CRTH2 receptor binding assay is performed in a scintillation proximity assay (SPA) format with the radioligand [$^3$H]-$PGD_2$ (Perkin Elmer, NET616000MC). CHO-K1-hCRTH2 cell membranes are again homogenized by passing through a single use needle (Terumo, 23G×1") and diluted in SPA incubation buffer in suitable concentrations (0.5-10 μg protein/well). The SPA assay is set up in 96 well microtiter plates (Perkin Elmer, Cat No. 6005040) in SPA incubation buffer with a final volume of 200 μL per well and final concentration of 50 mM Tris-HCl, 10 mM $MgCl_2$, 150 mM NaCl, 1 mM EDTA pH 7.4, 0.1% bovine serum albumin). The SPA assay mixture contains 60 μl of the membrane suspension, 80 μL of Wheat Germ Agglutinin coated PVT beads (GE Healthcare, RPNQ-0001, 0.3 mg/well), 40 μL of [$^3$H]-$PGD_2$ diluted in SPA buffer to a final concentration of 1 nM (50 000 dpm) and 20 μL of the test compound (dissolved in dimethylsulfoxide). The SPA assay mixture is incubated for 3 h at room temperature. Bound radioactivity is determined with a scintillation counter (Micro Beta Trilux, Wallac). The binding of [$^3$H]-$PGD_2$ to CHO-K1-hCRTH2 cell membranes is determined in the absence (total binding, Bo) and presence (non-specific binding, NSB) of unlabelled $PGD_2$ (1 μM, Cayman Chemical, Cat No 12010) or a reference CRTH2 antagonist (10 μM CAY10471, Cayman Chemical, Cat No 10006735). Determination of the affinity of a test compound is calculated by subtraction of the non-specific binding (NSB) from the total binding (Bo) or the binding in the presence of the test compound (B) at a given compound concentration. The NSB value is set to 100% inhibition. The Bo-NSB value is set to 0% inhibition.

% inhibition values were obtained at a defined compound concentration, e.g. at 1 μM, % inhibition of the test compound was calculated by the formula 100−((B−NSB)*100/(Bo−NSB)). % inhibition values above 100% are founded by assay variance.

The dissociation constant $K_i$ was calculated by iterative fitting of experimental data obtained at several compound concentrations over a dose range from 0.1 to 30 000 nM using the law of mass action based program "easy sys" (Schittkowski, Num Math 68, 129-142 (1994)).

CRTH2 Camp Functional Assay Protocol

The assay is conducted in CHO-K1-hCRTH2 cells. Intracellular cAMP is generated by stimulating the cells with 10 μM Forskolin, an adenylate cyclase activator. PGD2 is added to activate the CRTH2 receptor which results in the attenuation of the forskolin-induced cAMP generation. Test compounds are tested for their ability to inhibit the PGD2-mediated attenuation of the Forskolin-induced cAMP generation in CHO-K1-hCRTH2 cells. CHO-K1-hCRTH2 cells are cultured in roller bottles in CHO SFMII medium supplemented with 400 ug/mL G418. The cells are harvested by centrifugation at 300 g for 10 minutes at room temperature. The cell pellet is washed and suspended in PBS. The cells are adjusted to a final concentration of 4×10E6 cells/mL. Test compounds are diluted in dimethylsulfoxide and tested at several compound concentrations over a dose range from 0.1 to 3 000 nM.

The cAMP levels are determined by an AlphaScreen cAMP assay (Perkin Elmer Cat No. 6760625M) in 384 well optiplates (PerkinElmer, Cat No. 6007290) with a total assay volume of 50 μL. 10 μL of cells (40.000 cells per well) are incubated for 30 minutes at 37° C. with 10 μL of a stimulation mix containing a final concentration of 10 μM Forskolin, 30 nM PGD2, 0.5 mM IBMX, 5 mM HEPES, 1×HBSS buffer, 0.1% BSA, adjusted to pH 7.4, and the test compound at various concentrations. Thereafter, 30 μL of a lysis and detection mix is added containing SA donor beads, biotinylated cAMP, anti-cAMP acceptor beads, 0.3% Tween-20, 5 mM HEPES, 0.1% BSA, adjusted to pH 7.4. After 2 hours incubation time the AlphaScreen signal is read on an AlphaQuest-HTS instrument. The $IC_{50}$ values are calculated by using the Prism software.

Other CRTH2 Functional Assay Protocols

The ability of the tested compounds to antagonize the functional effects of PGD2 at the CRTH2 receptor may also be demonstrated by methodology known in the art, such as by a whole cell binding assay, a GTPgS assay, a BRET assay, an inositol phosphate accumulation assay, an CRTH2 cell surface expression assay, a $Ca^{2+}$ influx assay, an ERK phosphorylation assay, an cell migration assay, an eosinophil shape change assay, a Th2 cell degranulation assay, or a basophil activation assay as described by Mathiesen et al., Mol. Pharmacol. 2005, 68:393-402; Mimura et al., J. Pharmacol. Exp. Ther., 2005, 314:244-51; Sandham et al., Bioorg. Med. Chem. Lett., 2007, 17:4347-50; Sandham Bioorg. Med. Chem. Lett., 2009, 19:4794-8; Crosignani et al., J Med Chem, 2008, 51:2227-43; Royer et al., Eur J Clin Invest, 2008, 38:663-71; Boehme et al., Int Immunol, 2009, 21:621-32; Sugimoto et al., Pharmacol. Exp. Ther., 2003, 305:347-52; Monneret et al., J Pharmacol Exp Ther, 2005, 312:627-34; Xue et al., J. Immunol., 2005, 175:6531-6.

Cell lines for expressing the CRTH2 receptor include those naturally expressing the CRTH2 receptor, such as AML14.3D10 and NCI-H292 cells (Sawyer et al., Br. J. Pharmacol., 2002, 137:1163-72; Chiba et al., Int. Arch. Allergy. Immunol., 2007, 143 Suppl 1:23-7), those induced to express the CRTH2 receptor by the addition of chemicals, such as HL-60 or AML14.3D10 cells treated with, for example, butyric acid (Sawyer et al., Br. J. Pharmacol., 2002, 137: 1163-72) or a cell line engineered to express a recombinant CRTH2 receptor, such as L1.2, CHO, HEK-293, K562 or CEM cells (Liu et al., Bioorg. Med. Chem. Lett., 2009, 19:6840-4; Sugimoto et al., Pharmacol Exp Ther, 2003, 305: 347-52; Hata et al., Mol. Pharmacol., 2005, 67:640-7; Nagata et al., FEBS Lett, 1999, 459:195-9).

Finally, blood or tissue cells, for example human peripheral blood eosinophils, isolated using methods as described by Hansel et al., J. Immunol. Methods., 1991, 145, 105-110, or human Th2 cells isolated and treated as described by Xue et al., J. Immunol., 2005, 175:6531-6, or human basophils isolated and characterized as described by Monneret et al., J. Pharmacol. Exp. Ther., 2005, 312:627-34 can be utilized in such assays.

In particular, the compounds of the present invention have activity in binding to the CRTH2 receptor in the aforementioned assays and inhibit the activation of CRTH2 by CRTH2 ligands. As used herein, "activity" is intended to mean a compound demonstrating an inhibition of 50% at 1 μM or higher in inhibition, or a $K_i$ value <1 μM, when measured in the aforementioned assays. Such a result is indicative of the intrinsic activity of the compounds as inhibitor of CRTH2 receptor activity. Antagonistic activities of selected compounds are shown in tables 1 and 2 below.

TABLE 1

Compounds of formula Ia''

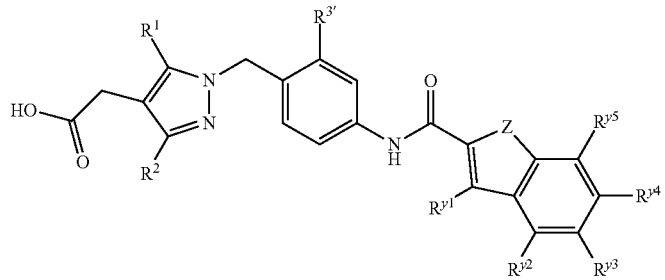

(Ia'')

| Cmpd | R3' | R1 = R2 | Z | Ry1; Ry2; Ry3; Ry4; Ry5 | MS [M + H]+ | Retention Time | Ki [nM] |
|---|---|---|---|---|---|---|---|
| 1 | F | CH3 | NH | H; H; H; H; H | 421 | 1.04 method G | 0.8 |
| 2 | Cl | CH3 | NH | H; H; H; H; H | 437 | 1.36 min method B | 0.5 |
| 3 | F | CH3 | NCH2—C6H5 | H; H; H; H; H | 511 | 0.98 min method D | 0.2 |
| 4 | H | CH3 | O | CH3; H; F; H; H | 436 | 0.85 min method D | 0.8 |
| 5 | Cl | CH3 | O | H; H; H; H; H | 438 | 0.86 min method D | 0.8 |
| 6 | H | CH3 | O | H; H; OCH3; H; H | 434 | 0.77 min method D | 0.6 |
| 7 | H | CH3 | O | CH3; H; H; H; F | 436 | 0.86 min method D | 1.3 |
| 8 | H | CH3 | O | H; H; Cl; H; H | 438 | 0.84 min method D | 0.3 |
| 9 | H | CH3 | O | H; H; H; H; OCH3 | 434 | 0.78 min method D | 1.2 |
| 10 | H | CH3 | NH | H; H; H; H; H | 403 | 1.24 min method B | 0.2 |
| 11 | H | CH3 | NH | H; H; H; F; H | 421 | 0.76 min method D | 0.2 |

TABLE 1-continued

Compounds of formula Ia''

(Ia'')

| Cmpd | R3' | R1 = R2 | Z | Ry1; Ry2; Ry3; Ry4; Ry5 | MS [M + H]+ | Retention Time | Ki [nM] |
|---|---|---|---|---|---|---|---|
| 12 | H | CH3 | NH | H; H; F; H; H | 421 | 0.76 min method D | 0.2 |
| 13 | H | CH3 | NCH3 | CH3; H; H; H; H | 431 | 0.81 min method D | 63.9 |
| 14 | H | CH3 | NH | CH3; H; OCH3; H; H | 447 | 0.79 min method D | 0.1 |
| 15 | H | CH3 | S | H; H; H; H; H | 420 | 1.32 min method B | 0.3 |
| 16 | H | CH3 | NCH3 | H; H; H; H; H | 417 | 1.29 min method K | 0.8 |
| 17 | H | CH3 | NC2H5 | H; H; H; H; H | 431 | 1.35 min method K | 0.4 |
| 18 | H | CH3 | NCH2—C6H5 | H; H; H; H; H | 493 | 0.88 min method D | <0.1 |
| 19 | H | C2H5 | O | H; H; Cl; H; H | 466 | 1.43 min method K | 0.2 |
| 20 | H | C2H5 | NH | H; H; H; H; H | 431 | 1.30 min method K | 0.3 |
| 21 | H | C2H5 | NCH3 | H; H; H; H; H | 445 | 0.84 min method D | 0.3 |
| 22 | H | C2H5 | NC2H5 | H; H; H; H; H | 459 | 0.87 min method D | 0.2 |
| 23 | H | C2H5 | NH | H; H; F; H; H | 449 | 0.80 min method D | 0.3 |
| 24 | H | C2H5 | NCH3 | CH3; H; H; H; H | 459 | 0.84 min method D | 9.9 |
| 25 | H | C2H5 | NH | H; H; H; F; H | 449 | 1.34 min method K | 0.2 |
| 26 | H | CH3 | O | H; H; H; H; H | 404 | 1.28 min method B | 0.8 |
| 27 | F | CH3 | O | CH3; H; F; H; H | 454 | 0.90 min method D | 0.6 |
| 28 | H | CH3 | N(CH2)2—CH3 | H; H; H; F; H | 463 | 0.85 min method E | 0.1 |
| 29 | H | CH3 | NC2H5 | H; H; H; F; H | 449 | 0.84 min method E | 0.1 |
| 30 | F | CH3 | NCH3 | H; H; H; H; H | 435 | 0.85 min method C | 1.0 |
| 31 | F | CH3 | NC2H5 | H; H; H; H; H | 449 | 0.85 min method C | 0.2 |
| 32 | F | CH3 | NC2H5 | H; H; F; H; H | 467 | 0.89 min method D | 0.2 |
| 33 | H | CH3 | O | CH3; H; H; H; Cl | 452 | 1.39 min method J | 2.2 |
| 34 | H | CH3 | O | CH2CH3; H; H; H; F | 450 | 1.38 min method L | 0.3 |
| 35 | H | CH3 | O | CH2CH3; H; F; H; F | 468 | 1.43 min method L | 0.3 |
| 36 | H | CH3 | O | H; H; H; Cl; H | 438 | 1.32 min method M | 0.2 |
| 37 | F | CH3 | O | CH3; H; H; H; Cl | 470 | 1.46 min method J | 2.2 |
| 38 | F | CH3 | O | CH2CH3; H; H; H; F | 468 | 0.88 min method E | 0.6 |
| 39 | F | CH3 | O | H; H; H; Cl; H | 456 | 1.40 min method M | 0.4 |
| 40 | F | CH3 | NC2H5 | H; F; H; H; H | 467 | 0.87 min method E | 0.4 |
| 41 | F | CH3 | NC2H5 | H; H; H; F; H | 467 | 0.87 min method E | 0.1 |

TABLE 1-continued

Compounds of formula Ia''

(Ia'')

| Cmpd | R³' | R¹ = R² | Z | Rʸ¹; Rʸ²; Rʸ³; Rʸ⁴; Rʸ⁵ | MS [M + H]⁺ | Retention Time | Ki [nM] |
|---|---|---|---|---|---|---|---|
| 42 | F | CH₃ | N(CH₂)₂—CH₃ | H; H; H; F; H | 481 | 0.89 min method E | 0.1 |
| 43 | F | CH₃ | O | CH₂OCH₃; H; H; H; H | 466 | 0.86 min method D | 2.3 |
| 44 | F | CH₃ | O | CH₃; H; Cl; H; H | 470 | 0.95 min method D | 0.3 |
| 45 | F | CH₃ | O | CH₃; H; Br; H; H | 514 | 0.96 min method D | 0.3 |
| 46 | F | CH₃ | S | CH₃; H; F; H; H | 470 | 0.88 min method D | 4.5 |
| 47 | F | CH₃ | O | CH₂CH₃; H; F; H; H | 468 | 0.94 min method D | 0.9 |
| 48 | H | CH₃ | O | CH₂CH₃; H; F; H; H | 450 | 0.85 min method E | 1.2 |
| 49 | F | CH₃ | O | CH₃; H; OCH₃; H; H | 466 | 1.30 min method F | 0.1 |
| 50 | F | CH₃ | O | CH₃; H; H; H; F | 454 | 1.32 min method F | 0.4 |
| 51 | F | CH₃ | NCH₃ | H; H; F; H; H | 453 | 1.28 min method F | 0.4 |
| 52 | F | CH₃ | O | (CH₂)₂CH₃; H; F; H; H | 482 | 0.87 min method D | 0.7 |
| 53 | F | CH₃ | N(CH₂)₃—CH₃ | H; H; H; H; H | 477 | 1.41 min method O | 0.2 |
| 54 | F | CH₃ | N(CH₂)₂—CH₃ | H; H; F; H; H | 481 | 0.92 min method D | 0.2 |
| 55 | F | CH₃ | N(CH₂)₃—CH₃ | H; H; F; H; H | 495 | 0.91 min method E | 0.1 |
| 56 | F | CH₃ | N(CH₂)₂—CH₃ | H; H; H; H; H | 463 | 0.87 min method E | 0.2 |

TABLE 2

Compounds of formula Ib''

(Ib'')

| Cmpd | R¹, R² | R³' | Z | Rʸ¹; Rʸ²; Rʸ³; Rʸ⁴; Rʸ⁵ | MS [M + H]⁺ | Retention Time | Ki [nM] |
|---|---|---|---|---|---|---|---|
| 57 | CH₃ | H | O | H; H; H; H; H | 404 | 1.29 min method B | 8.8 |

TABLE 2-continued

Compounds of formula Ib''

(Ib'')

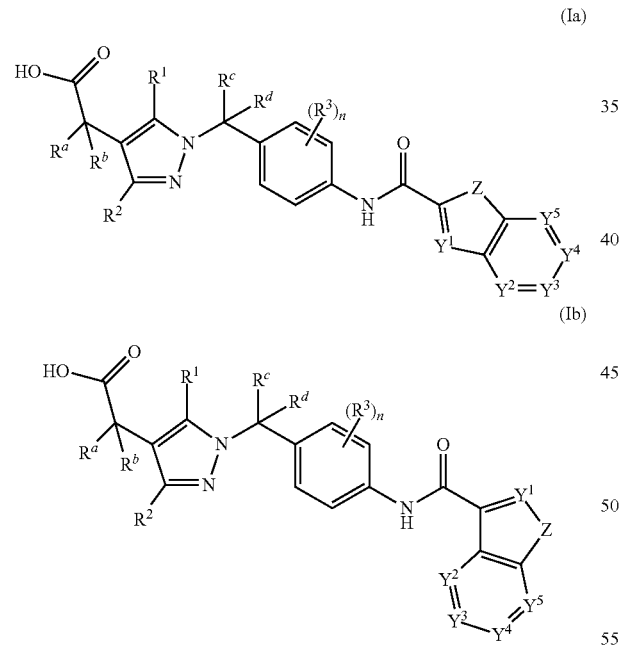

| Cmpd | $R^1, R^2$ | $R^{3'}$ | Z | $R^{y1}; R^{y2}; R^{y3}; R^{y4}; R^{y5}$ | MS [M + H]+ | Retention Time | Ki [nM] |
|---|---|---|---|---|---|---|---|
| 58 | $CH_3$ | H | NH | H; H; H; H; H | 403 | 1.14 min method B | 37.2 |
| 59 | $CH_3$ | H | S | H; H; H; H; H | 420 | 1.32 min method B | 3.8 |

The invention claimed is:

1. A pyrazole compound of formula (Ia) or (Ib) and pharmaceutically acceptable salts thereof, (Ia)

(Ib)

wherein:

$R^a$ and $R^b$ are each independently hydrogen, hydroxy, halogen, $C_1$-$C_6$-alkyl, $C_1$-$C_6$ haloalkyl, $C_1$-$C_6$-alkoxy, $C_1$-$C_6$-haloalkoxy, or $C_3$-$C_8$-cycloalkyl, or $R^a$ and $R^b$ together with the carbon atom they are bound to form a carbonyl group, or $R^a$ and $R^b$ together with the carbon atom they are bound to form a 3- to 8-membered ring, wherein the ring optionally contains 1 or 2 heteroatoms selected from O, N, and S as a ring member and wherein the ring members of the ring are optionally independently substituted by hydroxy, halogen, $C_1$-$C_6$-alkyl, $C_1$-$C_6$-haloalkyl, $C_1$-$C_6$-alkoxy, $C_1$-$C_6$-haloalkoxy, or $C_3$-$C_8$-cycloalkyl;

$R^c$ and $R^d$ are each independently hydrogen, hydroxy, halogen, $C_1$-$C_6$-alkyl, $C_1$-$C_6$-haloalkyl, $C_1$-$C_6$-alkoxy, $C_1$-$C_6$-haloalkoxy, or $C_3$-$C_8$-cycloalkyl, or $R^c$ and $R^d$ together with the carbon atom they are bound to form a carbonyl group, or $R^c$ and $R^d$ together with the carbon atom they are bound to form a 3- to 8-membered ring, wherein the ring optionally contains 1 or 2 heteroatoms selected from O, N, and S as a ring member and wherein the ring members of the ring are optionally independently substituted by hydroxy, halogen, $C_1$-$C_6$-alkyl, $C_1$-$C_6$-haloalkyl, $C_1$-$C_6$-alkoxy, $C_1$-$C_6$-haloalkoxy, or $C_3$-$C_8$-cycloalkyl;

$Y^1$, $Y^2$, $Y^3$, $Y^4$, and $Y^5$ are each independently N or $CR^y$, wherein each $R^y$ is independently H, hydroxy, halogen, cyano, nitro, $SF_5$, $C(O)NR^fR^g$, $C_1$-$C_6$-alkyl, hydroxy-$C_1$-$C_6$-alkyl, $C_1$-$C_6$-alkoxy-$C_1$-$C_6$-alkyl, $C_3$-$C_8$-cycloalkyl, $C_1$-$C_6$-haloalkyl, $C_1$-$C_6$-alkoxy, $C_1$-$C_6$-alkoxy-$C_1$-$C_6$-alkoxy, $C_1$-$C_6$-haloalkoxy, $C_3$-$C_8$-cycloalkoxy, $C_1$-$C_6$-alkylamino, di-$C_1$-$C_6$-alkylamino, $C_1$-$C_6$-alkylsulfonyl, phenyl, phenoxy, 5- or 6-membered heterocyclyl, or 5- or 6-membered heterocyclyloxy;

Z is O, S, or $NR^z$, wherein $R^z$ is H, $C_1$-$C_6$-alkyl, or benzyl;

$R^1$ and $R^2$ are each independently H, halogen, $C_1$-$C_6$-alkyl, $C_2$-$C_6$-alkenyl, $C_2$-$C_6$-alkynyl, $C_1$-$C_6$-alkoxy, $C_1$-$C_6$-alkylthio, —$NR^fR^g$, $C_3$-$C_8$-cycloalkyl, $C_3$-$C_8$-cycloalkyl-$C_1$-$C_6$-alkyl, $C_3$-$C_8$-cycloalkyl-$C_2$-$C_6$-alkenyl, $C_3$-$C_8$-cycloalkenyl, $C_3$-$C_8$-cycloalkenyl-$C_1$-$C_6$-alkyl, $C_3$-$C_8$-cycloalkenyl-$C_2$-$C_6$-alkenyl, phenyl, phenyl-$C_1$-$C_6$-alkyl, phenyl-$C_2$-$C_6$-alkenyl, naphthyl, naphthyl-$C_1$-$C_6$-alkyl, naphthyl-$C_2$-$C_6$-alkenyl, heterocyclyl, heterocyclyl-$C_1$-$C_6$-alkyl, or heterocyclyl-$C_2$-$C_6$-alkenyl, wherein the $C_1$-$C_6$-alkyl, $C_2$-$C_6$-alkenyl, and $C_2$-$C_6$-alkynyl moieties in $R^1$ and $R^2$ are unsubstituted or carry at least one substituent selected from hydroxy, halogen, cyano, nitro, $C_1$-$C_6$-alkoxy, $C_1$-$C_6$-haloalkoxy, $C_1$-$C_6$-alkylamino, di $C_1$-$C_6$-alkylamino, and $C_1$-$C_6$-alkylsulfonyl, and/or wherein two radicals bound to the same carbon atom of the $C_1$-$C_6$-alkyl, $C_2$-$C_6$-alkenyl, and $C_2$-$C_6$-alkynyl moieties in $R^1$ and $R^2$ together with the carbon atom optionally form a carbonyl group, and wherein the $C_3$-$C_8$-cycloalkyl, cycloalkenyl, phenyl, naphthyl, and heterocyclyl moieties in $R^1$ and $R^2$ are unsubstituted or carry at least one substituent selected from hydroxy, halogen, cyano, nitro, $C_1$-$C_6$-alkyl, $C_3$-$C_8$-cycloalkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, $C_1$-$C_6$-alkylsulfonyl, phenyl, and 5- or 6-membered hetaryl and/or wherein two radicals bound to the same carbon atom of the $C_3$-$C_8$-cycloalkyl, $C_3$-$C_8$-cycloalkenyl and heterocyclyl moieties of $R^1$ and $R^2$ together with the carbon atom optionally form a carbonyl group;

$R^f$ and $R^g$ are each independently H, $C_1$-$C_6$-alkyl, $C_1$-$C_6$-haloalkyl, $C_3$-$C_8$-cycloalkyl, $C_3$-$C_8$-cycloalkenyl, or 5- or 6-membered heterocyclyl, or $R^f$ and $R^g$ together with the nitrogen atom to which they are bound form a cyclic amine optionally comprising a further heteroatom selected from O, N, and S as a ring member;

n is 0, 1, 2, or 3; and $R^3$ are each independently halogen, $C_1$-$C_6$-alkyl, $C_1$-$C_6$-haloalkyl, $C_1$-$C_6$-alkoxy, $C_1$-$C_6$-haloalkoxy, or $C_3$-$C_8$-cycloalkyl.

2. The pyrazole compound of formula (Ia) or (Ib) according to claim 1, wherein $R^a$ and $R^b$ are both hydrogen.

3. The pyrazole compounds of formula (Ia) or (Ib) according to claim 1, wherein $R^c$ and $R^d$ are both hydrogen.

4. The pyrazole compounds of formula (Ia) or (Ib) according to claim 2, wherein $R^c$ and $R^d$ are both hydrogen.

5. The pyrazole compound of formula (Ia) or (Ib) according to claim 1, wherein $Y^1$ is $CR^{y1}$ and $R^{y1}$ is independently selected from $R^y$ as defined in claim 1.

6. The pyrazole compound of formula (Ia) or (Ib) according to claim 5, wherein $R^{y1}$ is H, $C_1$-$C_6$-alkyl, $C_1$-$C_6$-alkoxy-$C_1$-$C_6$-alkyl, or $C_1$-$C_6$-haloalkyl.

7. The pyrazole compound of formula (Ia) or (Ib) according to claim 5, wherein $Y^2$ is $CR^{y2}$, $Y^3$ is $CR^{y3}$, $Y^4$ is $CR^{y4}$, and $Y^5$ is $CR^{y5}$, wherein $R^{y2}$, $R^{y3}$, $R^{y4}$ and $R^{y5}$ are each independently selected from $R^y$.

8. The pyrazole compound of formula (Ia) or (Ib) according to claim 7, wherein $R^{y2}$, $R^{y3}$, $R^{y4}$, and $R^{y5}$ are each independently H, halogen, $C_1$-$C_6$-alkoxy, $C_1$-$C_6$-alkoxy-$C_1$-$C_6$-alkyl, or $C_1$-$C_6$-haloalkoxy.

9. The pyrazole compound of formula (Ia) or (Ib) according to claim 1, wherein Z is O.

10. The pyrazole compound of formula (Ia) or (Ib) according to claim 1, wherein Z is S.

11. The pyrazole compound of formula (Ia) or (Ib) according to claim 1, wherein Z is $NR^z$.

12. The pyrazole compound of formula (Ia) or (Ib) according to claim 1, wherein $R^1$ and $R^2$ are each independently H, $C_1$-$C_6$-alkyl, $C_3$-$C_8$-cycloalkyl, phenyl, or naphthyl.

13. The pyrazole compound of formula (Ia) or (Ib) according to claim 12, wherein $R^1$ and $R^2$ are each independently H, $C_1$-$C_4$-alkyl, $C_3$-$C_6$-cycloalkyl, or phenyl.

14. The pyrazole compound of formula (Ia) or (Ib) according to claim 13, wherein $R^1$ and $R^2$ are each independently $C_1$-$C_4$-alkyl.

15. The pyrazole compound of formula (Ia) or (Ib) according to claim 1, wherein n is 0 or 1.

16. The pyrazole compound of formula (Ia) or (Ib) according to claim 1, wherein $R^3$ are each independently halogen.

17. The pyrazole compound of formula (Ia) according to claim 7, wherein the pyrazole compound is a compound of formula (Ia')

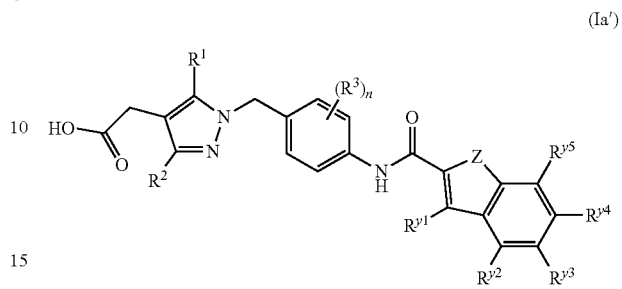

(Ia')

and n is 0 or 1.

18. The pyrazole compound of formula (Ib) according to claim 7, wherein the pyrazole compound is a compound of formula (Ib')

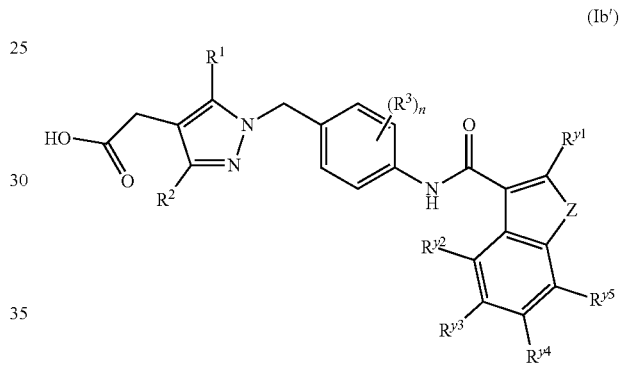

(Ib')

and n is 0 or 1.

19. A method of treating a disease that can be treated by inhibition of CRTH2 receptor in a patient in need thereof, the method comprising administering an effective amount of a pyrazole compound of formula (Ia) or (Ib) according to claim 1 to the patient.

20. A pharmaceutical formulation comprising a pyrazole compound of formula (Ia) and/or (Ib) according to claim 1 and a pharmaceutical excipient.

21. The pharmaceutical formulation of claim 20, further comprising a betamimetic, anticholinergic, corticosteroid, PDE4 inhibitor, LTD4 antagonist, EGFR inhibitor, CCR3 antagonist, CCR5 antagonist, CCR9 antagonist, 5-LO inhibitor, histamine-receptor antagonist, SYK inhibitor, or sulfonamide.

22. The pyrazole compound according to claim 9, wherein the pyrazole compound is (1-{4-[(5-fluoro-3-methylbenzofuran-2-carbonyl)amino]benzyl}-3,5-dimethyl-1H-pyrazol-4-yl)acetic acid or a pharmaceutically acceptable salt thereof.

23. The pyrazole compound according to claim 9, wherein the pyrazole compound is (1-{4-[(benzofuran-2-carbonyl)aminol-2-chlorobenzyl}-3,5-dimethyl-1H-pyrazol-4-yl)acetic acid or a pharmaceutically acceptable salt thereof.

24. The pyrazole compound according to claim 9, wherein the pyrazole compound is (1-{4- [(5-methoxybenzofuran-2-carbonyl)amino]benzyl}-3,5-dimethyl-1H-pyrazol-4-yl)-acetic acid or a pharmaceutically acceptable salt thereof.

25. The pyrazole compound according to claim 9, wherein the pyrazole compound is (1-{4-[(7-fluoro-3-methylbenzofuran-2-carbonyl)amino]benzyl}-3,5-dimethyl-1H-pyrazol-4-yl)acetic acid or a pharmaceutically acceptable salt thereof.

26. The pyrazole compound according to claim 9, wherein the pyrazole compound is (1-{[(5-chlorobenzofuran-2-carbonyl)amino]benzyl}-3,5-dimethyl-1H-pyrazol-4-yl)acetic acid or a pharmaceutically acceptable salt thereof.

27. The pyrazole compound according to claim 9, wherein the pyrazole compound is (1-{4- [(7-methoxybenzofuran-2-carbonyl)amino]benzyl}-3,5-dimethyl-1H-pyrazol-4-yl) acetic acid or a pharmaceutically acceptable salt thereof.

28. The pyrazole compound according to claim 9, wherein the pyrazole compound is (1-{4-[(5-chlorobenzofuran-2-carbonyl)amino]benzyl}-3,5-diethyl-1H-pyrazol-4-yl)acetic acid or a pharmaceutically acceptable salt thereof.

29. The pyrazole compound according to claim 9, wherein the pyrazole compound is (1-{4-[(benzofuran-2-carbonyl)amino]benzyl}-3,5-dimethyl-1H-pyrazol-4yl)acetic acid or a pharmaceutically acceptable salt thereof.

30. The pyrazole compound according to claim 9, wherein the pyrazole compound is (1-{4-[(5-fluoro-3-methylbenzofuran-2-carbonyl)amino]-2-fluorobenzyl}-3,5-dimethyl-1H-pyrazol-4-yl)acetic acid or a pharmaceutically acceptable salt thereof.

31. The pyrazole compound according to claim 9, wherein the pyrazole compound is (1-{4- [(7-chloro-3-methylbenzofuran-2-carbonyl)amino]benzyl}-3,5-dimethyl-1H-pyrazol-4-yl)acetic acid or a pharmaceutically acceptable salt thereof.

32. The pyrazole compound according to claim 9, wherein the pyrazole compound is (1-{4-[(3-ethyl-7-fluorobenzofuran-2-carbonyl)amino]benzyl}-3,5-dimethyl-1H-pyrazol-4-yl)acetic acid or a pharmaceutically acceptable salt thereof.

33. The pyrazole compound according to claim 9, wherein the pyrazole compound is (1-{4-[(5,7-difluoro-3-ethylbenzofuran-2-carbonyl)amino]benzyl}3,5-dimethyl-1H-pyrazol-4-yl)acetic acid or a pharmaceutically acceptable salt thereof.

34. The pyrazole compound according to claim 9, wherein the pyrazole compound is (1-{4- [(6-chlorobenzofuran-2-carbonyl)amino]benzyl}3,5-dimethyl-1H-pyrazol-4-yl)acetic acid or a pharmaceutically acceptable salt thereof.

35. The pyrazole compound according to claim 9, wherein the pyrazole compound is (1-{4- [(7-chloro-3-methylbenzofuran-2-carbonyl)amino]-2-fluorobenzyl}-3,5-dimethyl-1H-pyrazol-4-yl) acetic acid or a pharmaceutically acceptable salt thereof.

36. The pyrazole compound according to claim 9, wherein the pyrazole compound is (1-{4-[(3-ethyl-7-fluorobenzofuran-2-carbonyl)amino]-2-fluorobenzyl}-3,5-dimethyl-1H-pyrazol-4-yl)acetic acid or a pharmaceutically acceptable salt thereof.

37. The pyrazole compound according to claim 9, wherein the pyrazole compound is (1-{4-[(6-chlorobenzofuran-2-carbonyl)amino]-2-fluorobenzy}-3,5-dimethyl-1H-pyrazol-4-yl)acetic acid or a pharmaceutically acceptable salt thereof.

38. The pyrazole compound according to claim 9, wherein the pyrazole compound is (1-{4-[(methoxymethyl)benzofuran-2-carbonyl)amino]-2-fluorobenzyl}3,5-dimethyl-1H-pyrazol-4-yl)acetic acid or a pharmaceutically acceptable salt thereof.

39. The pyrazole compound according to claim 9, wherein the pyrazole compound is (1-{4-[(5-chloro-3-methylbenzofuran-2-carbonyl)amino]-2-fluorobenzyl}-3,5-dimethyl-1H-pyrazol-4-yl)acetic acid or a pharmaceutically acceptable salt thereof.

40. The pyrazole compound according to claim 9, wherein the pyrazole compound is (1-{4-[(5-bromo-3-methylbenzofuran-2-carbonyl)amino]-2-fluorobenzyl}-3,5-dimethyl-1H-pyrazol-4-yl)acetic acid or a pharmaceutically acceptable salt thereof.

41. The pyrazole compound according to claim 9, wherein the pyrazole compound is (1-{4-[(3-ethyl-5-fluorobenzofuran-2-carbonyl)amino]-2-fluorobenzyl}-3,5-dimethyl-1H-pyrazol-4-yl)acetic acid or a pharmaceutically acceptable salt thereof.

42. The pyrazole compound according to claim 9, wherein the pyrazole compound is (1-{4-[(3-ethyl-5-Fluorobenzofuran-2-carbonyl)amino]benzyl}-3,5-dimethyl-1H-pyrazol-4-yl)acetic acid or a pharmaceutically acceptable salt thereof.

43. The pyrazole compound according to claim 9, wherein the pyrazole compound is (1-{4-[(5-methoxy-3-methylbenzofuran-2-carbonyl)amino]-2-fluorobenzyl}-3,5-dimethyl-1H-pyrazol-4-yl)acetic acid or a pharmaceutically acceptable salt thereof.

44. The pyrazole compound according to claim 9, wherein the pyrazole compound is (1-{4-[(7-fluoro-3-methylbenzofuran-2-carbonyl)aminol]-2-fluorobenzyl}-3,5-dimethyl-1H-pyrazol-4-yl)acetic acid or a pharmaceutically acceptable salt thereof.

45. The pyrazole compound according to claim 9, wherein the pyrazole compound is (1-{4-[(5-fluoro-3-(n-propyl)benzofuran-2-carbonyl)amino]-2-fluorobenzyl}-3,5-dimethyl-1H-pyrazol-4-yl)acetic acid or a pharmaceutically acceptable salt thereof.

* * * * *